United States Patent
Itoh et al.

(10) Patent No.: US 6,362,206 B1
(45) Date of Patent: *Mar. 26, 2002

(54) AZOLE COMPOUNDS, THEIR PRODUCTION AND USE

(75) Inventors: Katsumi Itoh; Kenji Okonogi; Akihiro Tasaka, all of Osaka (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/413,876

(22) Filed: Oct. 7, 1999

Related U.S. Application Data

(62) Division of application No. 08/624,649, filed as application No. PCT/JP96/00325 on Feb. 15, 1996, now Pat. No. 6,034,248.

(30) Foreign Application Priority Data

Feb. 17, 1995 (JP) ............................................. 7-029579
Nov. 1, 1995 (JP) ............................................. 7-285318

(51) Int. Cl.$^7$ .................... A61K 31/4192; C07D 403/14
(52) U.S. Cl. ...................... 514/359; 514/383; 548/255; 548/266.6
(58) Field of Search .......................... 548/255; 514/359

(56) References Cited

U.S. PATENT DOCUMENTS

| | | | |
|---|---|---|---|
| 5,677,464 A | 10/1997 | Itoh et al. | 548/264.6 |
| 5,792,780 A | 8/1998 | Itoh et al. | 514/383 |
| 6,034,248 A | * 3/2000 | Itoh et al. | 548/253 |

FOREIGN PATENT DOCUMENTS

| | | |
|---|---|---|
| EP | 0 122 056 A1 | 10/1984 |
| EP | 0 122 693 A1 | 10/1984 |
| EP | 0 332 387 A1 | 9/1989 |
| EP | 0548 553 | 6/1993 |
| EP | 0 567 982 A1 | 11/1993 |
| EP | 0 657 449 A1 | 6/1995 |
| EP | 0 659 751 A1 | 6/1995 |
| EP | 0 687 672 | 12/1995 |
| GB | 2 159 148 A | 11/1985 |
| WO | WO 95/22973 | 8/1995 |

OTHER PUBLICATIONS

Cram, et al., "Organic Chemistry" McGraw Hill Book Co., NY (1964) 2nd ed. pp 565–567.

* cited by examiner

Primary Examiner—Patricia L. Morris
(74) Attorney, Agent, or Firm—Foley & Lardner

(57) ABSTRACT

The present invention provides an azole compound represented by the formula (I):

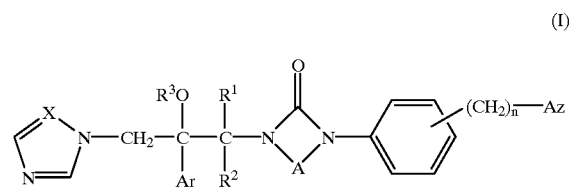

wherein Ar is an optionally substituted phenyl group; $R^1$ and $R^2$, the same or different, are a hydrogen atom or a lower alkyl group, or $R^1$ and $R^2$ may combine together to form a lower alkylene group; R is a hydrogen atom or an acyl group; X is a nitrogen atom or a methine group; A is Y=Z (Y and Z, the same or different, are a nitrogen atom or a methine group optionally substituted with a lower alkyl group) or an ethylene group optionally substituted with a lower alkyl group; n is an integer from 0 to 2; and Az is an optionally substituted azolyl group, or its salt, which is useful for a prevention and therapy of a fungal infection of a mammal as a antifungal agent.

11 Claims, No Drawings

AZOLE COMPOUNDS, THEIR PRODUCTION AND USE

This application is a division of U.S. application Ser. No. 08/624,649, filed Oct. 17, 1996, now U.S. Pat. No. 6,034,248, which was the National Stage of International Application No. PCT/JP96/00325, filed Feb. 15, 1996.

TECHNICAL FIELD

The present invention relates to azole compounds useful as antifungal therapeutic agents, methods for producing the same and use thereof.

BACKGROUND ART

A variety of azole compounds have been reported exhibiting antifungal activity (see, for example, EP0122056A1, EP0332387A1, EP0122693A1 and EP0567982A).

None of these azole compounds, however, is satisfactory as a pharmaceutical agent in terms of its antifungal activity, antifungal spectrum, side effect and in vivo pharmacokinetics.

There has been a demand for a safer compound which exhibits better absorption in vivo and higher antifungal activity as an antifungal therapeutic agent.

DISCLOSURE OF INVENTION

The present invention provides (1) a compound represented by the formula (I):

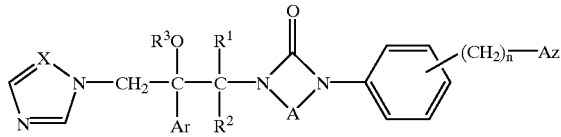

wherein Ar is an optionally substituted phenyl group; $R^1$ and $R^2$, the same or different, are a hydrogen atom or a lower alkyl group, or $R^1$ and $R^2$ may combine together to form a lower alkylene group; $R^3$ is a hydrogen atom or an acyl group; X is a nitrogen atom or a methine group; A is Y=Z (Y and Z, the same or different, are a nitrogen atom or a methine group optionally substituted with a lower alkyl group) or an ethylene group optionally substituted with a lower alkyl group; n is an integer from 0 to 2; and Az is an optionally substituted azolyl group, or a salt thereof, (2) a process for preparing a compound of the formula (I) as defined in claim 1 or a salt thereof which comprises
(i) reacting a compound represented by the formula (II):

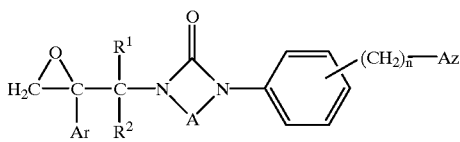

wherein the symbols have the same meanings as defined above; or a salt thereof with a compound represented by the formula (III):

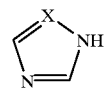

wherein the symbols have the same meanings as defined above; or a salt thereof, and, if necessary, followed by an acylation;
(ii) reacting a compound represented by the formula (IV):

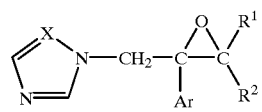

wherein the symbols have the same meanings as defined above; or a salt thereof
with a compound represented by the formula (V'):

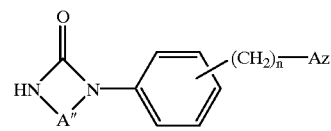

wherein A" is —N=CH—, —CH=N— or —CH=CH—; the symbols have the same meanings as defined above; or a salt thereof, and, if necessary, followed by an acylation; or
(iii) reducing a compound represented by the formula (I")

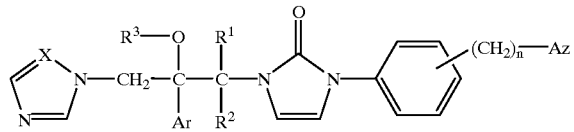

wherein the symbols have the same meanings as defined above; or a salt thereof, and, if necessary, followed by an acylation, (3) a pharmaceutical composition to be an antifungal preparation containing a compound represented by the above formula (I) or a salt thereof.

Examples of the substituents for "optionally substituted phenyl group" represented by Ar in the formula (I) include halogen atoms (e.g., fluorine, chlorine, bromide and iodine), lower ($C_{1-4}$) haloalkyl, lower ($C_{1-4}$) haloalkoxy, lower ($C_{1-4}$) alkylsulfonyl, lower ($C_{1-4}$) haloalkylsulfonyl and the like. Preferably, the substituent is halogen atoms (e.g., fluorine, chlorine, bromine and iodine), and more preferably it is fluorine. The number of the substituents is preferably from one to three, more preferably from one to two.

Examples of Ar include halophenyl, lower ($C_{1-4}$) haloalkylphenyl, lower ($C_{1-4}$) haloalkoxyphenyl, lower ($C_{1-4}$) alkylsulfonylphenyl, lower ($C_{1-4}$) haloalkylsulfonylphenyl and the like.

Examples of the halophenyl groups include 2,4-difluorophenyl, 2,4-dichlorophenyl, 4-chlorophenyl, 4-fluorophenyl, 2-chlorophenyl, 2-fluorophenyl, 2-fluoro-4-chlorophenyl, 2-chloro-4-fluorophenyl, 2,4,6-trifluropheny, 4-bromophenyl and the like.

Examples of the lower ($C_{1-4}$) haloalkylphenyl groups include 4-trifluoromethylphenyl group and the like.

Examples of the lower ($C_{1-4}$) haloalkoxyphenyl groups include 4-trifluoromethoxyphenyl, 4-(1,1,2,2-tetrafluoroethoxy)phenyl, 4-(2,2,2-trifluoroethoxy)phenyl, 4-(2,2,3,3-tetrafluoropropoxy)phenyl, 4-(2,2,3,3,3-pentafluoropropoxy)phenyl and the like.

Examples of the lower ($C_{1-4}$) alkylsulfonylphenyl groups include 4-methanesulfonylphenyl and the like.

Examples of the lower ($C_{1-4}$) haloalkylsulfonylphenyl groups include 4-(2,2,2-trifluoroethanesulfonyl)phenyl, 4-(2,2,3,3-tetrafluoropropanesulfonyl)phenyl, 4-(2,2,3,3,3-pentafluoropropanesulfonyl)phenyl and the like.

Specific examples of the phenyl groups of Ar are phenyl groups substituted with one to two halogen atoms such as 2,4-difluorophenyl, 2,4-dichlorophenyl, 4-chlorophenyl, 4-fluorophenyl, 2-chlorophenyl, 2-fluorophenyl, 2-fluoro-4-chlorophenyl, 2-chloro-4-fluorophenyl, 4-bromophenyl and the like, among which phenyl groups substituted with one or two fluorine atoms such as 4-fluorophenyl, 2-fluorophenyl and 2,4-difluorophenyl are more preferable and 2-fluorophenyl and 2,4-difluorophenyl are most preferable.

Examples of the lower alkyl groups represented by $R^1$ or $R^2$ in the formula (I) include straight or branched $C_{1-4}$ alkyl groups such as methyl, ethyl, propyl, isopropyl, butyl, isobutyl, sec-butyl, tert-butyl and the like, among which methyl is more preferable. It is particularly preferable that both of $R^1$ and $R^2$ are hydrogen atoms or methyl groups, or one of $R^1$ and $R^2$ is a hydrogen atom and the other is a methyl group.

Examples of the lower alkylene groups formed by the combination of $R^1$ and $R^2$ include straight lower ($C_{2-4}$) alkylene groups such as ethylene, propylene, butylene and the like, among which ethylene is preferred.

Among them, it is preferable that one of $R^1$ and $R^2$ is a hydrogen atom and the other is a $C_{1-4}$ alkyl group such as a methyl group and the like.

Examples of the acyl groups represented by $R^3$ in the formula (I) include acyl groups derived from organic carboxylic acids such as alkanoyl, preferably $C_{1-7}$ alkanoyl (e.g., formyl, acetyl, propionyl, butyryl, isobutyryl, pentanoyl, hexanoyl and heptanoyl), more preferably $C_{1-3}$ alkanoyl; arylcarbonyl, preferably $C_{7-15}$ arylcarbonyl (e.g., benzoyl and naphtalenecarbonyl), more preferably $C_{7-11}$ arylcarbonyl group; alkoxycarbonyl, preferably $C_{2-7}$ alkoxycarbonyl (e.g., methoxycarbonyl, ethoxycarbonyl, propoxycarbonyl, isopropoxycarbonyl, butoxycarbonyl, isobutoxycarbonnyl, sec-bu-toxycarbonyl and tert-butoxycarbonyl), more preferably $C_{2-4}$ alkoxycarbonyl; aryloxycarbonyl, preferably $C_{7-15}$ aryloxy-carbonyl (e.g., phenoxycarbonyl), more preferably $C_{7-11}$ aryloxycarbonyl; aralkylcarbonyl group, preferably $C_{8-20}$ aralkylcarbonyl (e.g., benzylcarbonyl, phenetylcarbonyl, phenylpropylcarbonyl and naphthylethylcarbonyl), more preferably $C_{8-14}$ aralkylcarbonyl; and the like.

Preferably, the above acyl groups are those being capable of hydrolyzing in vivo. Examples thereof are formyl, acetyl, benzoyl, benzylcarbonyl and the like. Preferred $R^3$ is a hydrogen atom.

X in the general formula (I) is preferably a nitrogen atom.

Examples of the lower alkyl groups for "a methine group optionally substituted by a lower alkyl group" represented by Y or Z when A is Y=Z in the formula (I) include straight or branched $C_{1-4}$ alkyl groups (methyl, ethyl, n-propyl, isopropyl, n-butyl, isobutyl, sec-butyl and tert-butyl), among which methyl is preferred.

Examples for the methine group optionally substituted with a lower alkyl group represented by Y or Z include methine, ethylidyne (—C(CH$_3$)=), propylidyne (—C(CH$_2$CH$_3$)=), butylidyne (—C(CH$_2$CH$_2$CH$_3$)=) and the like, among which methine, ethylidyne and the like are preferable, and methine and the like are more preferable.

It is preferable that one of Y and Z is a nitrogen atom and the other is methine; that both are methine; that both are nitrogen atoms; and one is a nitrogen atom and the other is ethylidyne. It is particularly preferable that one of Y and Z is a nitrogen atom and the other is methine or both of Y and Z are methine.

When A is "an ethylene group optionally substituted with a lower alkyl group" in the formula (I), examples of the lower alkyl groups include straight or branched $C_{1-4}$ alkyl groups (methyl, ethyl, n-propyl, isopropyl, n-butyl, isobutyl, sec-butyl and tert-butyl), among which methyl, ethyl and the like are preferable, and methyl and the like are more preferable.

Examples of the ethylene groups optionally substituted with a lower alkyl group represented by A include ethylene, 1-methylethylene, 1,1-dimethylethylene, 1,2-dimethylethylene, 1-ethylethylene, 1,2-diethylethylene and the like, among which ethylene and the like are preferred.

Specific examples of A are —N=CH—, —CH=N—, —CH=CH—, —N=N—, —N=C(CH$_3$)—, —C(CH$_3$)=N—, —CH$_2$—CH$_2$— and the like, among which —N=CH—, —CH=N—, —CH=CH—, —CH$_2$—CH$_2$— and the like are preferred.

In the formula (I), the groups represented by

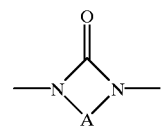

are preferably

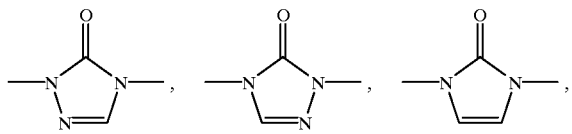

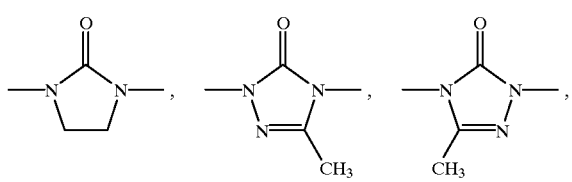

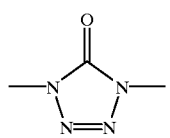

and the like, more preferably

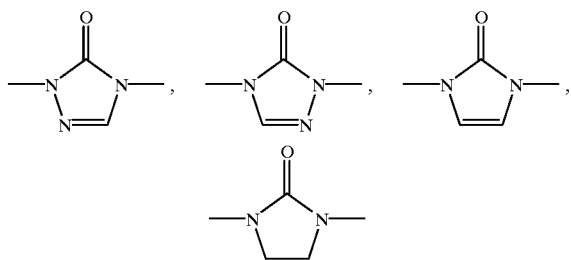

and the like, still more preferably

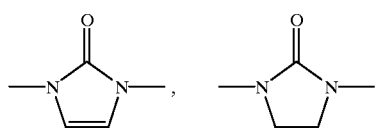

and the like.

The integer from 0 to 2 represented by n is preferably 0 or 1, more preferably 0.

Examples of the azolyl groups for "an optionally substituted azolyl group" represented by Az in the formula (I) include five-membered aromatic heterocyclic groups containing one to four nitrogen atoms as ring-constituent atoms, which may further contain a hetero atom selected from sulfur or oxygen as a ring-constituent atom, such as pyrrolyl, pyrazolyl, imidazolyl, 1,2,3-triazolyl, 1,2,4-triazolyl, tetrazolyl, thiazolyl, isothiazolyl, oxazolyl, isoxazolyl, furazanyl, 1,3,4-thiadiazolyl, 1,2,3-thiadiazolyl, 1,2,5-thiadiazolyl, 1,2,4-thiadiazolyl and the like.

In particular, the azolyl groups are preferably pyrazolyl, imidazolyl, 1,2,3-triazolyl, 1,2,4-triazolyl, tetrazolyl and the like, more preferably 1H-pyrazol-1-yl, 1H-imidazol-1-yl, 1H-1,2,3-triazol-1-yl, 2H-1,2,3-triazol-2-yl, 1H-1,2,4-triazol-1-yl, 4H-1,2,4-triazol-4-yl, 1H-tetrazol-1-yl, 2H-tetrazol-2-yl and the like, and further more preferably 1H-pyrazol-1-yl, 1H-1,2,3-triazol-1-yl, 2H-1,2,3-triazol-2-yl, 1H-1,2,4-triazol-1-yl, 1H-tetrazol-1-yl, 2H-tetrazol-2-yl and the like.

Examples of the substituents for "an optionally substituted azolyl group" represented by the above Az include hydroxyl group, optionally esterified carboxyl group (e.g., carboxyl, $C_{1-6}$ alkoxycarbonyl such as methoxycarbonyl, ethoxycarbonyl and butoxycarbonyl), nitro group, amino group, acylamino group (e.g., $C_{1-10}$ alkanoylamino such as acetylamino, propionylamino and butyrylamino), mono-$C_{1-10}$ or di-$C_{1-10}$ alkylamino group (e.g., methylamino, dimethylamino, diethylamino and dibutylamino), $C_{1-6}$ alkyl group (e.g., methyl, ethyl, propyl, isopropyl, butyl, tert-butyl, sec-butyl, pentyl and hexyl), $C_{1-6}$ alkoxy group (e.g., methoxy, ethoxy and butoxy), halogen atom (e.g., fluorine, chlorine and bromine), $C_{1-6}$ haloalkyl group (e.g., trifluoromethyl, dichloromethyl, 2,2,2-trifluoroethyl and 2,2,3,3-tetrafluoropropyl), $C_{1-6}$ haloalkoxy group (e.g., trifluoromethoxy, 1,1,2,2-tetrafluoroethoxy, 2,2,2-trifluoroethoxy, 2,2,3,3-tetrafluoropropoxy, 2,2,3,3,3-pentafluoropropoxy, 2,2,3,3,4,4,5,5-octafluoropentoxy and 2-fluoroethoxy), oxo group, thioxo group, mercapto group, $C_{1-6}$ alkylthio group (e.g., methylthio, ethylthio and butylthio), $C_{1-6}$ alkylsulfonyl group (e.g., methanesulfonyl, ethanesulfonyl and butanesulfonyl), $C_{1-10}$ alkanoyl group (e.g., acetyl, formyl, propionyl and butylyl), phenyl group, $C_{1-6}$ alkylphenyl group (e.g., p-tolyl, mesityl and p-cumenyl), $C_{1-6}$ alkoxyphenyl group (e.g., 4-methoxyphenyl and 4-isopropoxyphenyl), halophenyl group (e.g., 4-chlorophenyl and 4-fluorophenyl, 2,4,-difluorophenyl), $C_{1-6}$ haloalkylphenyl group [e.g., 4-trifluoromethylphenyl), $C_{1-6}$ haloalkoxyphenyl group (e.g., 4-trifluoromethoxyphenyl, 4-(2,2,3,3-tetrafluoropropoxy)-phenyl and 4-(1,1,2,2-tetrafluoroethoxy)phenyl] and the like. These substituents may be substituted on the ring-constituent carbon and/or nitrogen atom(s) of the azolyl group and the number of the substituents is preferably one or two.

Specifically, Az are preferably diazolyl, triazolyl and tetrazolyl such as

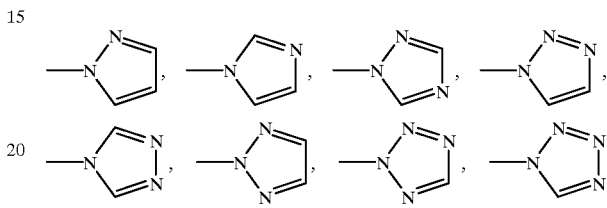

and the like, more preferably

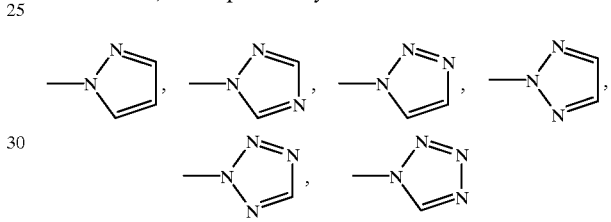

and the like.

A preferred example of the compound (I) is a compound represented by the formula (I')

(I')

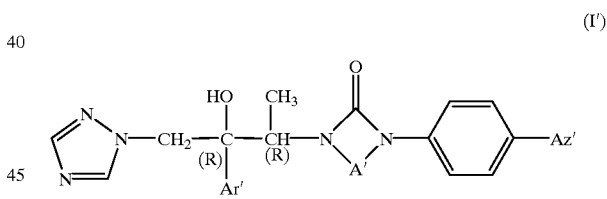

(wherein Ar' is a monofluorophenyl (e.g., 2-fluorophenyl) or difluorophenyl (e.g., 2,4-difluorophenyl) group; A' is —N=CH—, —CH=CH— or CH$_2$—CH$_2$—; and Az' is an azolyl group selected from the group consisting of a diazolyl, triazolyl, tetrazolyl, thiazolyl or oxazolyl which are optionally substituted with one or two substituents selected from the group consisting of an oxo group, a $C_{1-6}$ alkyl group (e.g., methyl, ethyl, n-propyl, iso-propyl), a $C_{1-6}$ haloalkyl group (e.g., trifluoromethyl, 2,2,2-trifluoroethyl, 2,2,3,3-tetrafluoropropyl) and a $C_{1-6}$ haloalkyloxyphenyl group (e.g., 4-trifluoromethoxyphenyl, 4-(2,2,3,3-tetrafluoropropoxyphenyl, 4-(1,1,2,2-tetrafluoroethoxyphenyl)) or a salt thereof. In the formula (I'), A' is preferably —CH$_2$—CH$_2$—, and Az' is preferably a triazolyl group and a tetrazolyl group.

The compound represented by the formula (I), (I') may be used as a salt thereof. Examples of such salts are pharmacologically acceptable salts such as inorganic acid salts (e.g., hydrochloride, hydrobromide, sulfate, nitrate and phosphorate), organic acid salts (e.g., acetate, tartarate, citrate, fumarate, maleate, toluenesulfonate and methanesulfonate). When carboxyl group is included in the formula (I) as a substituent, it may be an alkali methal (sodium, pottasium and the like) salt.

The compounds represented by the formula (I) or a salt thereof (hereinafter abbreviated as the compound of the present invention) have two or more stereoisomers thereof because of having one or more asymmetric carbon atom in their molecule. It should be understood that any of such stereoisomers as well as a mixture thereof is within a scope of the present invention. Among those, when $R^1$ is hydrogen and $R^2$ is methyl, both the carbon atom to which the optionally substituted phenyl group represented by Ar is bonded and the carbon atom to which $R^2$ is bonded are preferred to be in (R)-configuration.

The compound of the present invention can be produced by, for example, reacting a compound represented by the formula (II):

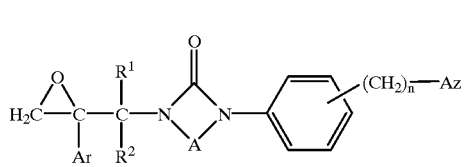

(II)

(wherein the symbols have the same meanings as defined above) or a salt thereof with a compound represented by the formula (III):

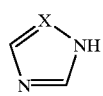

(III)

(wherein the symbols have the same meanings as defined above) or a salt thereof. This reaction provides a compound of the present invention in which $R^3$ is a hydrogen atom.

The reaction can be carried out in a solvent which does not inhibit the reaction. Examples of the solvents are water, ketones (e.g., acetone), sulfoxides (e.g., dimethyl sulfoxide), ethers (e.g., diethyl ether, tetrahydrofuran and dioxane), nitrites (e.g., acetonitrile), aromatic hydrocarbons (e.g., benzene, toluene and xylene), halogenated hydrocarbons (e.g., dichloromethane, chloroform and 1,2-dichloroethane), esters (e.g., ethyl acetate), amides (e.g., dimethylformamide, acetamide, dimethylacetamide and 1-methyl-2-pyrrolidinone), ureylenes (e.g., 1,3-dimetyl-2-imidazolidinone) and the like. These solvents may be used either singly or as a mixture of two or more solvents in a suitable mixing ratio.

Further, the reaction is preferably carried out in the presence of a base such as alkali metal hydroxides (e.g., lithium hydroxide, potassium hydroxide and sodium hydroxide), alkali metal hydrides (e.g., potassium hydride and sodium hydride), alkali metal carbonates (e.g., lithium carbonate, sodium bicarbonate, cesium carbonate, potassium carbonate and sodium carbonate), organic acid salts (e.g., sodium acetate), alkali metal alcoholates (e.g., sodium methylate, potassium tert-butylate and sodium tert-butylate), tetrabutylammonium fluoride, bis(tri-n-butylstannyl)oxide and the like.

Alternatively, the desired compound can also be prepared by the reaction in the above solvent using a metal salt (e.g., alkali metal salt such as sodium and potassium salt) of the compound (III) instead of the compound (III).

The amount of the base used is usually about 0:01 to at 100 equivalents, preferably about 0.1 to about 50 equivalents per equivalent of the compound of formula (III) or a salt thereof.

The amount of the compound (III) or a salt thereof is about 1 to about 100 equivalents, preferably about 1 to about 50 equivalents per equivalent of the compound of formula (II) or a salt thereof.

The reaction temperature is not especially limited, but usually within the range of about 0 to about 150° C., preferably about 10 to about 120° C.

The reaction time is usually within the range of about several minutes to tens of hours (e.g., from five minutes to fifty hours).

In another embodiment, the compound of the present invention can also be prepared by, for example, reacting a compound represented by the formula (IV):

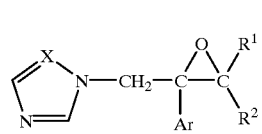

(IV)

(wherein the symbols have the same meanings as defined above) or a salt thereof
with a compound represented by the formula (V'):

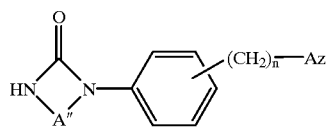

(V')

(wherein A" is —N=CH—, —CH=N— or —CH=CH—, the other symbols have the same meanings as defined above) or a salt thereof. The compound of the formula (V') may be a compound represented by the formula (V"):

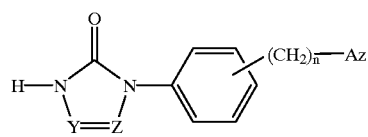

(V")

(wherein the symbols have the same meanings as defined above) or a salt thereof. This reaction provides a compound of the present invention which A is Y=Z and $R^3$ is hydrogen.

The reaction is usually carried out in a solvent which does not inhibit the reaction. Examples of the solvents are water, ketones (e.g., acetone), sulfoxides (e.g., dimethyl sulfoxide), ethers (e.g., diethyl ether, tetrahydrofuran and dioxane), nitrites (e.g., acetonitrile), aromatic hydrocarbons (e.g., benzene, toluene and xylene), halogenated hydrocarbons (e.g., dichloromethane, chloroform and 1,2-dichloroethane), esters (e.g., ethyl acetate), amides (e.g., dimethylformamide, acetamide, dimethylacetamide and 1-meth-yl-2-pyrrolidinone), ureylenes (e.g., 1,3-dimetyl-2-imidazolidinone) and the like. These solvents may be used either singly or as a mixture of two or more solvents in a suitable mixing ratio.

Further, the reaction is preferably carried out in the presence of a base such as alkali metal hydroxides (e.g., lithium hydroxide, potassium hydroxide, sodium hydroxide), alkali metal hydrides (e.g., potassium hydride and sodium hydride), alkali metal carbonates (e.g., lithium carbonate, sodium bicarbonate, cesium carbonate, potassium carbonate and sodium carbonate), organic acid salts (e.g., sodium acetate), alkali metal alcoholates (e.g., sodium methylate, potassium tert-butylate and sodium tert-butylate), tetrabutylammonium fluoride, bis(tri-n-butylstannyl)oxide and the like.

Alternatively the desired compound can also be prepared by the reaction in the above solvent using a metal salt (e.g., alkali metal salt such as sodium and potassium salt) of the compound (V') or (V") instead of the compound (V') or (V").

The amount of the base used is usually about 0.01 to about 100 equivalents, preferably about 0.1 to about 50 equivalents per equivalent of the compound of formula (V') or a salt thereof or (V") or a salt thereof.

The amount of compound (V') or (V") or a salt thereof is about 1 to about 100 equivalents, preferably about 1 to about 50 equivalents per equivalent of the compound of formula (IV) or a salt thereof.

The reaction temperature is not especially limited, but usually within the range of about 0 to about 150° C., preferably about 10 to about 120° C.

The reaction time is usually within the range of about several minutes to tens of hours (e.g., from five minutes to fifty hours).

According to another embodiment, the compound of the present invention can be prepared by, for example, reacting a compound represented by the formula (VI):

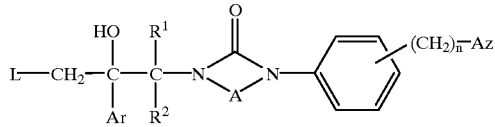
(VI)

{wherein L is a leaving group [e.g., halogen atom (e.g., chlorine, bromine and iodine) or $R^4SO_3$ (wherein $R^4$ is lower ($C_{1-4}$) alkyl group or optionally substituted phenyl group)] and the other symbols have the same meaning as defined above} or a salt thereof with a compound represented by the formula (III):

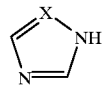
(III)

(wherein the symbols have the same meaning as defined above) or a salt thereof. This reaction provides a compound of the formula (I) in which $R^3$ is hydrogen.

Examples of the $C_{1-4}$ lower alkyl group represented by $R^4$ are methyl, ethyl, propyl, butyl and tert-butyl.

Examples of the optionally substituted phenyl group are the same as those of the optionally substituted phenyl group represented by Ar.

The reaction is usually carried out in a solvent which does not inhibit the reaction. Examples of the solvents are water, ketones (e.g., acetone), sulfoxides (e.g., dimethyl sulfoxide), ethers (e.g., diethyl ether, tetrahydrofuran and dioxane), nitriles (e.g., acetonitrile), aromatic hydrocarbons (e.g., benzene, toluene and xylene), halogenated hydrocarbons (e.g., dichloromethane, chloroform and 1,2-dichloroethane), esters (e.g., ethyl acetate), amides (e.g., dimethylformamide, acetamide, dimethylacetamide and l-methyl-2-pyrrolidinone), ureylenes (e.g., 1,3-dimetyl-2-imidazolidinone) and the like. These solvents may be used either singly or as a mixture of two or more solvents in a suitable mixing ratio.

Further, the reaction is preferably carried out in the presence of a base such as alkali metal hydroxides (e.g., lithium hydroxide, potassium hydroxide and sodium hydroxide), alkali metal hydrides (e.g., potassium hydride and sodium hydride), alkali metal carbonates (e.g., lithium carbonate, sodium bicarbonate, cesium carbonate, potassium carbonate and sodium carbonate), organic acid salts (e.g., sodium acetate), alkali metal alcoholates (e.g., sodium methylate, potassium tert-butylate and sodium tertbutylate), tetrabutylammonium fluoride, bis(tri-n-butylstannyl)oxide and the like.

Alternatively the desired compound can be prepared by the reaction in the above solvent using a metal salt (e.g., alkali metal salt such as sodium and potassium salt) of the compound (III) instead of the compound (III).

The amount of the base used is usually within the range of about 2 to about 100 equivalents, preferably about 2 to about 50 equivalents per equivalent of the compound of formula (III) or a salt thereof.

The amount of the compound (III) or a salt thereof is usually within the range of about 1 to about 100 equivalents, preferably about 1 to about 50 equivalents per equivalent of the compound of formula (VI) or a salt thereof.

The reaction temperature is not especially limited, but usually about 0 to about 150° C., preferably about 10 to about 120° C.

The reaction time is about tens of minutes to tens of hours (e.g., from thirty minutes to fifty hours).

The compound of the present invention wherein A is an ethylene group optionally substituted with a lower alkyl or salt thereof can be prepared by, for example, subjecting to a catalytic reduction a compound of the formula (I"):

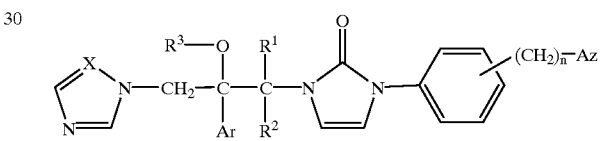
I"

(wherein the symbols have the same meaning as defined above) or a salt thereof, or the compound of the formula (I) wherein Y and Z are methine groups optionally substituted with lower alkyl (i.e., a compound (I''')):

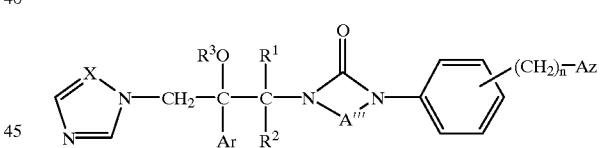
I'''

(wherein A''' is a vinylene group optionally substituted with lower alkyl group and the other symbols have the same meanings as defined above) or a salt thereof.

The above-mentioned reaction is usually carried out in the presence of a single or mixed solvent(s) such as water and organic solvents which do not inhibit the reaction such as ketones (e.g., acetone and methylethyl ketone), alcohols (e.g., methanol, ethanol, propanol, isopropyl alcohol and butanol), esters (e.g., ethyl acetate), hydrocarbons (e.g., benzene, toluene, hexane and xylene), organic carboxylic acids (e.g., acetic acid and propionic acid) and the like. The reaction is usually carried out in presence of catalyst. A suitable metal catalyst such as palladium-carbon is used as the catalyst. The reduction reaction is carried out at a pressure from atmospheric pressure up to about 150 kg/cm$^2$ at a temperature from room temperature up to about 100° C.

Examples of the salts of the above starting compounds (II), (IV), (VI), (I") and (I''' ) are the same as those of the compounds (I).

When a compound or a salt thereof of the present invention wherein $R^3$ is a hydrogen atom is obtained in the above reactions, the obtained compound or a salt thereof can be converted into by the conventional method to provide a compound of the formula (I) wherein $R^3$ is an acyl group, by treating it with an appropriate acylating agent of $R^3L^1$ [wherein $R^3$ is an aliphatic or aromatic carboxylic acid residue (e.g., acetyl, propionyl, butylyl, ethoxycarbonyl, benzoyl, substituted benzoyl) and $L^1$ is group to be removed (e.g., a halogen atom such as chlorine, bromine and the like, an active ester)] in accordance with the conventional method.

The above-mentioned reaction is usually carried out in the presence or absence of a solvent which does not inhibit the reaction. Examples of such solvents are water, ketones such as acetone, sulfoxides such as dimethyl sulfoxide, ethers such as diethyl ether, tetrahydrofuran and dioxane, nitriles such as acetonitrile, aromatic hydrocarbons such as benzen, toluene and xylene, halogenated hydrocarbons such as dichloromethane, chloroform and 1,2-dichloroethane, esters such as ethyl acetate, amides such as dimethylformamide, acetamide, dimethylacetamide, ureylenes such as 1,3-dimethyl-2-imidazolidinone, and the like. Also a base (e.g., dimethylaminopyridine, pyridine, pyrroline and triethylamine) may be added to the reaction system for acceleration of the reaction. The amount of the base used is usually about 1 to about 100 equivalents per equivalent of the compound of formula (I) or a salt thereof.

The compound of the present invention obtained as above can be isolated and purified from the reaction mixture by a known procedure per se such as extraction, concentration, neutralization, filtration, recrystallization, column chromatography, thin layer chromatography and the like.

The compound of the present invention may have at least two stereoisomers as mentioned above. Such a stereoisomer can be separately prepared if desired. For example, a single isomer can be obtained by the above reaction using each single isomer of the starting compounds (II), (IV), (VI), (I") and (I''') or salts thereof. Alternatively, when the obtained product is a mixture of two or more isomers, they can be separated into each isomer by the conventional separating method such as a method for producing a salt with an optically-active acid (e.g., camphorsulfonic acid and tartaric acid), various types of chromatographies, fractional recrystallization and the like.

The salt of the compound of the present invention can be prepared by a known method per se such as adding the aforesaid inorganic or organic acid to the compound (I).

The starting compound (II) or a salt thereof in the present invention wherein $R^1$ is hydrogen, $R^2$ is methyl, the carbon atom to which Ar is bonded is an (S)-configuration and the carbon atom to which $R^2$ is bonded is an (R)-configuration [i.e., a compound (VII) or a salt thereof] can be prepared, for example, by a method represented by the following reaction scheme:

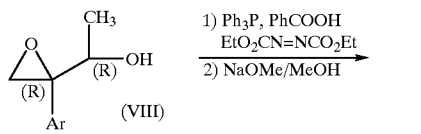

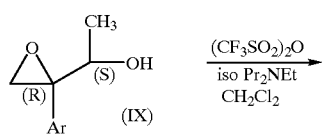

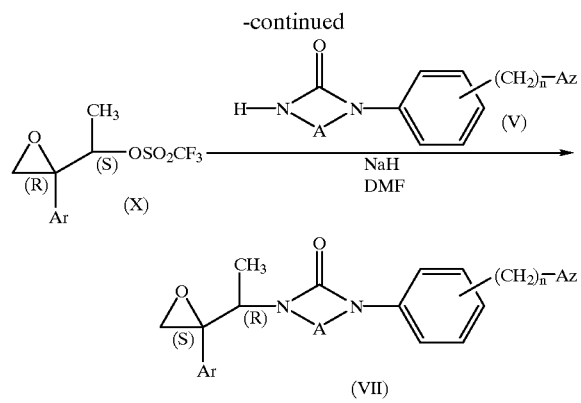

(wherein Me is methyl, Et is ethyl, Pr is propyl, Ph is phenyl, (R) and (S) denote the respectively symbolized configurations of the carbon atoms, DMF is dimethylformamide, and the other symbols have the same meanings as defined above).

The starting compound (VIII) in the reaction can be prepared, for example, by a method represented by the following reaction scheme:

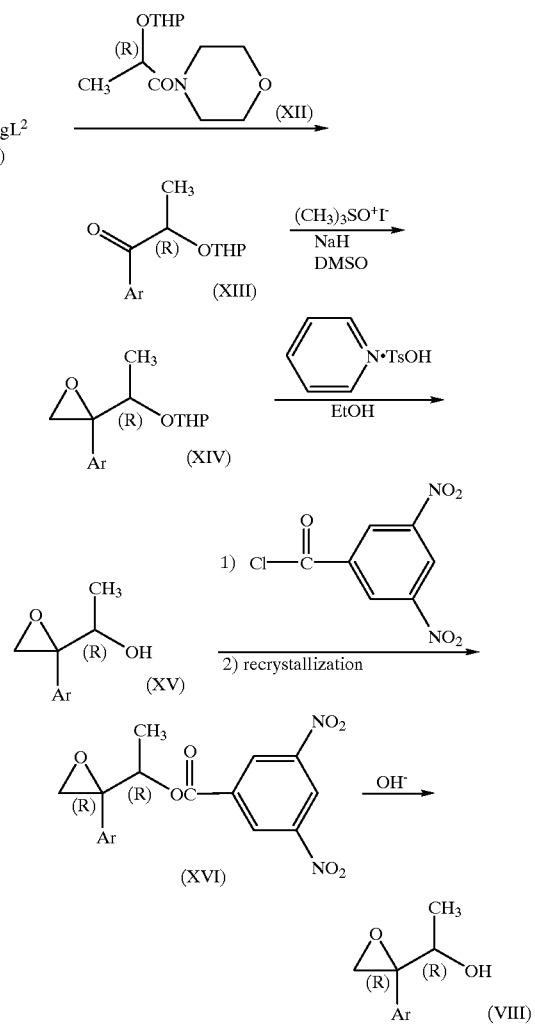

[wherein THP is tetrahydropyranyl group, Ts is p-toluenesulfonyl group, $L^2$ is a halogen atom (e.g., chlorine, bromine, iodine), DMSO is dimethylsulfoxide, and the other symbols have the same meanings as defined above].

The intermediate compound (IX) can be synthesized, for example, by a method represented by the following reaction scheme:

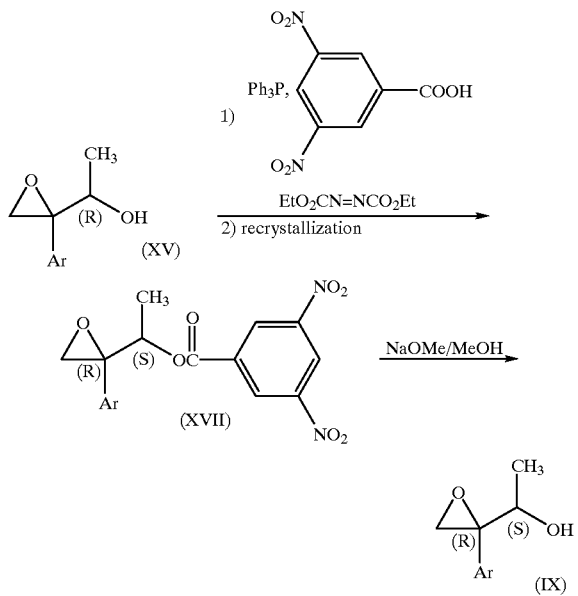

wherein the symbols have the same meanings as defined above).

The starting compound (IV) in the present invention wherein $R^1$ is a hydrogen atom, $R^2$ is a methyl group, the carbon atom to which Ar is bonded is in an (R)-configuration and the carbon atom to which $R^2$ is bonded is in an (S)-configuration [i.e., a compound (XVIII)]:

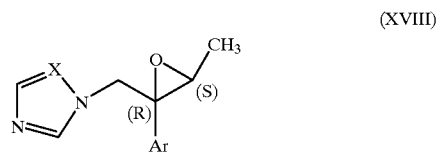

(XVIII)

(wherein the symbols have the same meanings as defined above) can be synthesized, for example, by methods described in EP0421210A, EP0548553A or EP0567982A or by a method based thereon.

The starting compound (VI) or a salt thereof in the present invention wherein $R^1$ is a hydrogen atom, $R^2$ is a methyl group, the carbon atom to which Ar is bonded in (S)-configuration, the carbon atom to which $R^2$ is bonded in (R)-configuration, and L is a leaving group represented by $R^4SO_3$ (wherein $R^4$ has the same meaning as mentioned above) [i.e., a compound (XIX) or a salt thereof], and the starting compound (II) or a salt thereof in the present invention wherein $R^1$ is a hydrogen atom, $R^2$ is a methyl group, the carbon atom to which Ar is bonded in (S)-configuration and the carbon atom to which $R^2$ is bonded in (R)-configuration [i.e., a compound (VII) or a salt thereof] can be prepared, for example, by a method represented by the following reaction scheme:

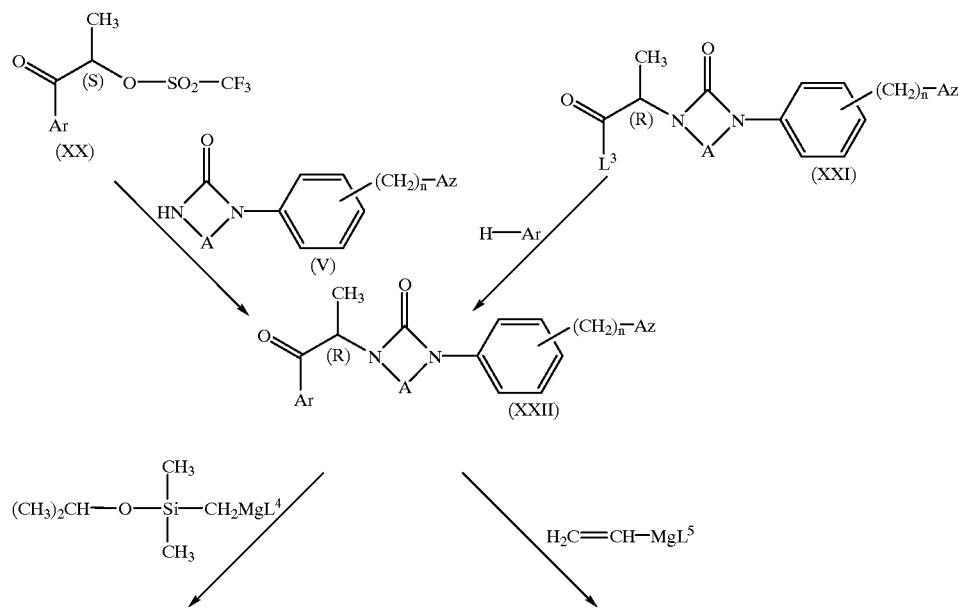

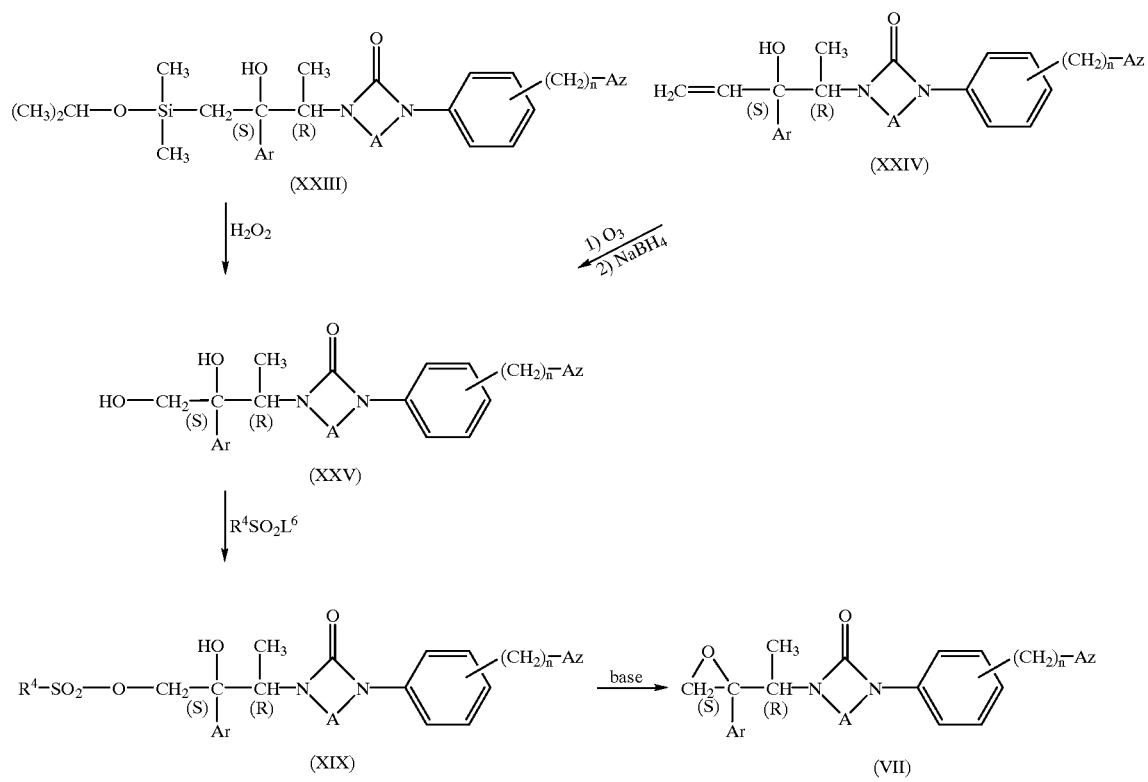

[wherein each of $L^3$, $L^4$, $L^5$ and $L^6$ is a halogen atom (e.g., chlorine, bromine, iodine) and the other symbols have the same meanings as defined above].

The starting compound (XX) or a salt thereof and the starting compound (XXI) or a salt thereof in the above reaction wherein $L^3$ is a chlorine atom [i.e., a compound (XXVI) or a salt thereof] can be each prepared, for example, by a method represented by the following reactions scheme:

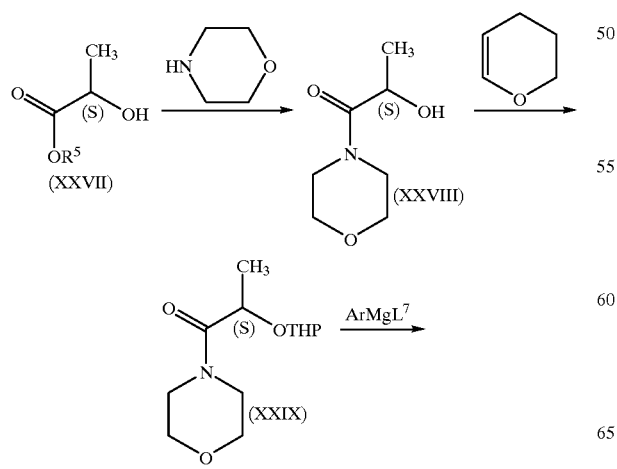

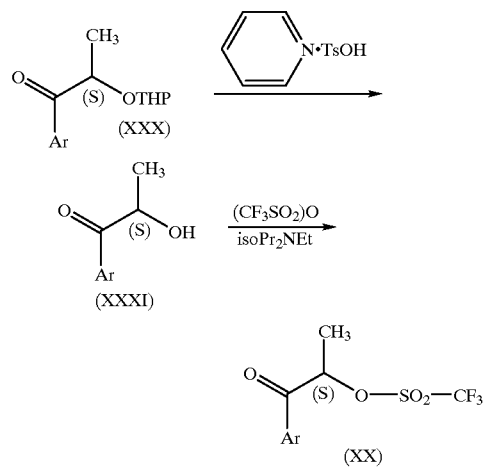

[wherein $R^5$ is a lower alkyl group, $L^7$ is a halogen atom (e.g., chlorine, bromine, iodine) and the other symbols have the same meanings as defined above].

A synthesizing method for a compound (XXXI) or a salt thereof in which Ar is 2,4-difluorophenyl as mentioned in the above reaction scheme is described in Japanese Patent Laid-Open No. HEI 5(1993)-230038.

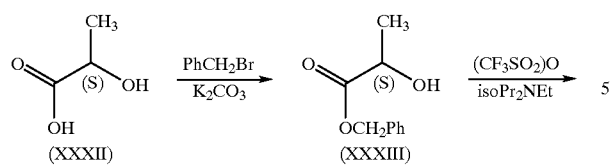

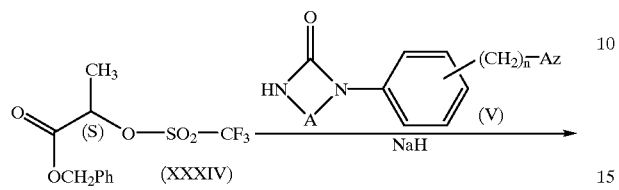

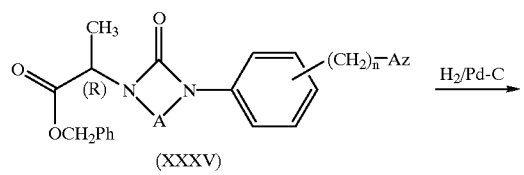

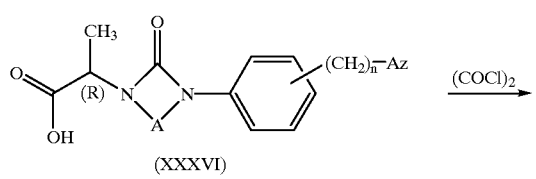

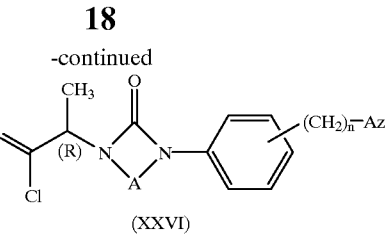

(wherein H$_2$/Pd-C denotes a catalytic reduction using palladium-carbon catalyst and the other symbols have the same meanings as defined above).

A compound (XXI) or a salt thereof wherein L$^3$ is a halogen atom except chlorine can be prepared using the corresponding halogenating agent [e.g., (COBr)$_2$, PBr$_3$] instead of (COCl)$_2$ in a similar way to the above reaction.

The starting compounds (V) or a salt thereof in the present invention wherein A is —N=CH—, —CH=CH— or —CH$_2$—CH$_2$—[i.e., compounds (XXXVII), (XXXVIII) and (XXXIX) or salts thereof respectively] can be prepared, for example, by the method represented by the following reaction scheme:

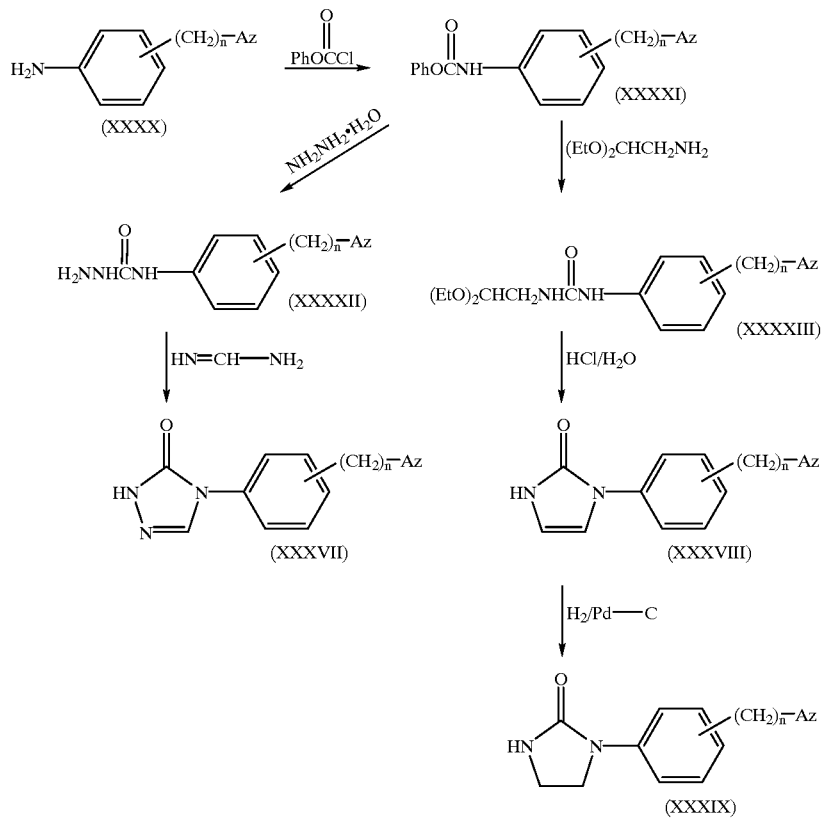

(wherein the symbols have the same meanings as defined above).

Further, the starting compound (V) or a salt thereof wherein A is —CH=N— [i.e., a compound (XXXXIV) or a salt thereof] can be prepared, for example, by a method represented by the reaction scheme:

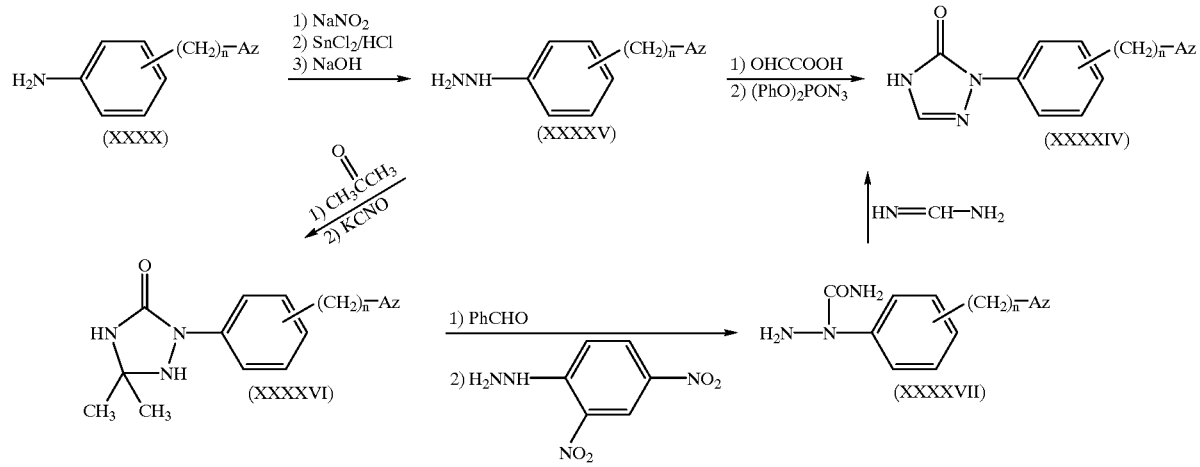

(wherein the symbols have the same meanings as defined above).

The starting compounds or synthesized intermediate compounds above-obtained can be isolated and purified from the reaction mixtures by a known procedure per se such as extraction, concentration, neutralization, filtration, recrystallization, column chromatography, thin layer chromatography and the like. Alternatively the reactant mixture itself can be used as a material in the next step without isolation.

The compound of the present invention has low toxicity and exhibits potent antifungal activity with broad antifungal spectrum against, for example, microorganisms of genus Candida (e.g., Candida albicans, Candida utilis, Candida grabrata, etc.), those of genus Histoplasma (e.g., Histoplasma capsulatum, etc.), those of genus Aspergillus (e.g., Aspergillus niger, Aspergillus fumigatus, etc.), those of genus Cryptococcus (e.g., Cryptococcus neoformans, etc.), those of genus Tricophyton (e.g., Trichophyton rubrum, Trichophyton mentagrophytes, etc.), those of genus Microsporum (e.g., Microsporum gypseum, etc.), those of genus Malassezia (e.g., Malassezia furfur, etc.) and the like. Accordingly, it can be used for prevention and treatment of the systemic fungal infection and dermatomycosis (e.g., candidiasis, histoplasmosis, aspergillosis, cryptococcosis, trichophytosis and microsporumosis) of mammals (e.g., human being, domestic animals and fowls) and further atopic dermatitis. Further, the compound of the invention can be used as an antifungal agent for agricultural use.

When the compound of the present invention is administered to a human being, it can be safely administered either orally or parenterally in the form of pharmaceutical compositions such as oral administration preparations (e.g., powders, granules, tablets, capsules), parenteral preparations [e.g., injections and external preparations (e.g., nasal and dermatological ones), suppositories (e.g., rectal and vaginal ones)] and the like in per se or in mixture with suitable pharmacologically-acceptable carriers, fillers or diluents. The content of the compound of the present invention in a whole pharmaceutical composition is usually 5 to 100 wt %, preferably 20 to 100 wt % in an oral drug and 5 to 30 wt % in a parenteral drug.

Those preparations can be manufactured by methods which are known per se and commonly used in the manufacture of pharmaceutical preparations.

For example, the compound of the present invention can be made into an injection such as aqueous injections together with dispersing agents [e.g., Tween 80 (Atlas Powder, U.S.A.), HCO60 (Nikko Chemicals, Japan), carboxymethylcellulose or sodium alginate], preservatives (e.g., methylparaben, propylparaben, benzyl alcohol and chlorobutanol), isotonic agents (e.g., sodium chloride, glycerol, sorbitol and glucose) and the like, or as oily injections by dissolving, suspending or emulsifying in a plant oil (e.g., olive oil, sesame oil, peanut oil, cotton seed oil and corn oil), propylene glycol and the like.

In the manufacture of preparations for oral administration, the compound of the present invention is compression-molded together, for example, with fillers (e.g., lactose, sugar and starch), disintegrating agents (e.g., starch and calcium carbonate), binders (e.g., starch, arabic gum, carboxymethylcellulose, polyvinylpyrrolidone and hydroxypropylcellulose), lubricants (e.g., talc, magnesium stearate and polyethylene glycol 6000) and the like, followed, if necessary, by coating in accordance with a known method per se with an object of taste-masking or of providing the preparation with enteric or sustained release property. Examples of the coating agents are hydroxypropylmethylcellulose, ethylcellulose, hydroxymethycellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (Rohm, West Germany; a copolymer of methacrylic acid with acrylic acid) and pigments such as titanium oxide and red iron oxide.

The compound of the present invention can be also used solid, semisolid or liquid preparations for external use. For example, in the case of solid external preparation, the compound of the present invention is made into the form of powdered compositions as it is or in a mixture with filler (e.g., glucose, mannitol, starch and microcrystalline cellulose), thickeners (e.g., natural gum, cellulose derivatives and acrylic acid polymers) and the like. In the case of semisolid external preparation, aqueous or oily gel preparation or ointment is preferred. In the case of liquid external preparation, the procedures are nearly the same as those in the case of injections to give oily or aqueous suspensions. pH Adjusting agents (e.g., carbonic acid, phosphoric acid, citric acid, hydrochloric acid and sodium hydroxide), antiseptics (e.g., p-hydroxybenzoates, chlorobutanol and benzalkonium chloride) or the like can be added to the above-mentioned solid, semisolid or liquid preparations. More specifically, it can be used for sterilization of disinfection of skin or mucous membrane as an ointment containing, for example, about 0.1 to 100 mg of the compound of the present invention per gram using Vaseline (petroleum jelly) or lanolin as a base material.

The compound of the present invention can be made into oily or aqueous solid, semisolid or liquid suppositories. Examples of the oily base materials used therefor are higher fatty acid glycerides [e.g., cacao butter and Witepsols (Dynamite-Nobel)], medium fatty acids (e.g., Migriols (Dynamite-Nobel)] or plant oil (e.g., sesame oil, soybean oil and cotton seed oil) and the like. Examples of the aqueous base materials are polyethylene glycols, propylene glycols, and those of the aqueous gel base materials are natural gums, cellulose derivatives, vinyl polymers, acrylic acid polymers.

The dose of the compound of the present invention may vary depending upon the state of infection, the route of administration or the like. In the case of orally administrating it to an adult patient (weight: 50 kg) for the therapy of candidiasis, for example, it is about 0.01 to 100 mg/kg/day and, preferably about 0.1 to 50 mg/kg/day, and more preferably about 1 to 20 mg/kg/day.

When the compound of the present invention is used as an agricultural antifungal agent, it may be dissolved or dispersed in a suitable liquid carrier (e.g., solvents), or mixed or absorbed with a suitable solid carrier (e.g., diluents and fillers), followed, if necessary, by addition of an emulsifier, suspending agent, spreader, penetrating agent, moisturizing agent, thickener, stabilizer, etc. to give the preparation a form such as emulsion, hydrating agent, powder, granules and the like. Such preparations can be prepared by known methods per se. The amount of the compound of the present invention is, for example, about 25 to 150 g, preferably about 40 to 80 g per acre of irrigated rice field for prevention of rice blast diseases.

Examples of the above liquid carrier are water, alcohols (e.g., methyl alcohol, ethyl alcohol, n-propyl alcohol, isopropyl alcohol and ethylene glycol), ethers (e.g., dioxane, tetrahydrofran), aliphatic hydrocarbons (e.g., kerosene, lamp oil and fuel oil), aromatic hydrocarbons (e.g., benzene and toluene), haloganated hydrocarbons (e.g., methylene chloride and chloroform), acid amides (e.g., dimethylformamide and dimethylacetamido), esters (e.g., ethyl acetate and butyl acetate), nitrils (e.g., acetonitrile and propionitrile) and the like. They may be used either singly or as a mixture thereof in a suitable mixture ratio.

Examples of the above solid carriers are plant powder (e.g., soybean powder, tobacco powder and wheat flour), mineral powder (e.g., kaolin and bentonite), alumina, sulfur powder, activated charcoal and the like. They may be used either individually or as a mixture thereof in a suitable mixing ratio.

BEST MODE FOR CARRYING OUT THE INVENTION

The present invention is further described by way of the following Reference Examples and Working Examples.

$^1$H-NMR spectra were measured by a spectrometer of Varian Gemini 200 type (200 MHz) using tetramethylsilane as an internal standard. All δ values are given by ppm. In the mixing solvents, the figures given in ( ) are the mixing ratio of each of the solvents by volume. Unless otherwise specified, the symbol % means by weight. In the silica gel chromatography, the ratio of the solvents is a ratio of the mixed solvents by volume.

The symbols used in the examples have the following meanings.

s: singlet; d: doublet; t: triplet; q: quartet; dd: double doublet; tt: triple triplet; m: multiplet; br: broad; J: coupling constant.

REFERENCE EXAMPLE 1

2-(2,4-Difluorophenyl)-2-[(1R)-1-(3,4,5,6-tetrahydro-2H-pyran-2-yl)oxyethyl]oxirane (82 g) (synthesized by the method disclosed in Japanese Unexamined Patent Publication No. Hei 4(1992)-74168) and pyridinium p-toluenesulfonate (6.3 g) were dissolved in ethanol (600 ml), and the resultant was stirred at 55° C. for 1 hour and concentrated under reduced pressure. The residue was dissolved in ethyl acetate (1 lit.) and washed with water (200 ml×2). The aqueous layer was extracted with ethyl acetate (100 ml×2). The combined organic layers were washed with a saturated aqueous solution of sodium chloride, dried over magnesium sulfate and distilled under reduced pressure to remove the solvent. The residue was purified by silica gel chromatography (eluent: hexane/ethyl acetate=10/1 to 8/1 to 3/1) to give (1R)-1-[2-(2,4-difluorophenyl)-2-oxiranyl] ethanol (31.5 g) as a pale yellow oily substance.

$^1$H-NMR (CDCl$_3$)δ: 1.14–1.23 (3H,m), 1.77, 2.22 (1H), 2.80, 2.92 (1H), 3.27–3.32 (1H), 4.00–4.20 (1H,m), 6.75–6.94 (2H,m), 7.36–7.48 (1H,m).

REFERENCE EXAMPLE 2

(1R)-1-[2-(2,4-Difluorophenyl)-2-oxiranyl]ethanol (31.5 g) and 3,5-dinitrobenzoyl chloride (40 g) were dissolved in methylene chloride (500 ml), to which trimethylamine (24.1 ml) was added dropwise at ice-bath temperature. After the mixture was stirred at room temperature for 3.5 hours, it was washed with water (150 ml) and 5% sodium bicarbonate aqueous solution successively, dried over magnesium sulfate and concentrated under reduced pressure. The precipitated crystals were filtrated and washed with methylene chloride. The mother liquor and the washings were combined and distilled off under reduced pressure. Ethyl acetate (25 ml) and methanol (300 ml) were added to the residue, and the mixture was cooled in an ice bath. The precipitated crystals were collected by filtration and recrystallized from a mixture of ethyl acetate (25 ml) and methanol (250 ml) to give [(1R)-1-[(2R)-2-(2,4-difluorophenyl)-2-oxiranyl]ethyl] 3,5-dinitrobenzoate (28.7 g) as colorless needles.

mp: 104–107° C. (recrystallized from ethylacetate-hexane) $^1$H-NMR (CDCl$_3$)δ: 1.46 (3H,dd,J=6.6 Hz,J=1.2 Hz), 3.01 (1H,d,J=4.6 Hz), 3.23 (1H,d,J=4.6 Hz), 5.33 (1H,q,J=6.6 Hz), 6.85–7.07 (2H,m), 7.54 (1H,m), 9.13 (2H, d,J=2.2 Hz), 9.25 (1H,t,J=2.2 Hz).

REFERENCE EXAMPLE 3

[(1R)-1-[(2R)-2-(2,4-Difluorophenyl)-2-oxiranyl]ethyl] 3,5-dinitrobenzoate (50 g) was dissolved in methanol (2 lit.), to which 1N-sodium hydroxide (255 ml) was added dropwise at room temperature. The mixture was stirred at room temperature for 1 hour and neutralized by an addition of 1 N-hydrochloric acid (127 ml) thereto. The resultant was concentrated under reduced pressure, to which ethyl acetate (1 lit.) and water (200 ml) were added. The mixture was extracted with ethyl acetate. The organic layer was washed with a saturated aqueous solution of sodium chloride (200 ml), dried over magnesium sulfate and distilled under reduced pressure to remove the solvent. The residue was purified by silica gel chromatography (eluent: ethyl acetate/hexane=1/3) to give (1R)-1-[(2R)-2-(2,4-difluorophenyl)-2-oxiranyl]ethanol (25 g) as a pale yellow oily substance.

$^1$H-NMR (CDCl$_3$)δ: 1.17 (3H,dd,J=6.6 Hz,1.2 Hz), 1.83 (1H,d,J=8 Hz), 2.80 (1H,d,J=5.2 Hz), 3.30 (1H,d,J=5.2 Hz), 4.01–4.17 (1H,m), 6.75–6.93 (2H,m) 7.36–7.48 (1H,m).

REFERENCE EXAMPLE 4

To an ice-cooled solution of (1R)-1-[(2R)-2-(2,4-difluorophenyl)-2-oxiranyl]ethanol (16.1 g) in tetrahydrofuran (320 ml) were added triphenylphosphine (63.3 g), benzoic acid (29.5 g) and diethyl azodicarboxylate (42.0 g). The mixture was stirred at room temperature for 6 hours under an argon atmosphere. After ethyl acetate (800 ml) and water (500 ml) were added thereto, the separated aqueous layer was extracted with ethyl acetate (200 ml). The combined organic layers were washed with water and a saturated aqueous solution of sodium chloride successively, dried over magnesium sulfate and concentrated. The residue was purified by silica gel chromatography (eluent: hexane/ethyl acetate=15/1 to 7/1) to give [(1S)-1-[(2R)-2-(2,4-difluorophenyl)-2-oxiranyl]ethyl] benzoate (19.2 g) as a colorless oily substance.

$^1$H-NMR (CDCl$_3$)δ: 1.37 (3H,d,J=6.6 Hz), 2.90 (1H,d,J=5.2 Hz), 3.28 (1H,d,J=5.2 Hz), 5.36 (1H,q,J=6.6 Hz), 6.74–6.94 (2H,m), 7.38–7.60 (4H,m), 7.94–8.01 (2H,m); IR ν max$^{neat}$ cm$^{-1}$: 1725, 1615, 1600, 1505, 1450, 1425.

[(1S)-1-[(2R)-2-(2,4-Difluorophenyl)-2-oxiranyl]-ethyl] benzoate (15.9 g) was dissolved in methanol (800 ml), to which 28% sodium methylate-methanol solution (12.9 ml) was added at ice-bath temperature and stirred at room temperature for 6 hours. After 1N-hydrochloric acid (63.2 ml) was added thereto, the solvent was distilled off under reduced pressure. The residue was purified by silica gel chromatography (eluent: hexane/ethyl acetate=6/1 to 2/1) to give (1S)-1-[(2R)-2-(2,4-difluorophenyl)-2-oxiranyl]ethanol (9.7 g) as a colorless oily substance.

$^1$H-NMR (CDCl$_3$)δ: 1.20 (3H,dd,J=6.4 Hz,1 Hz), 2.24 (1H,d,J=2 Hz), 2.92 (1H,d,J=5 Hz), 3.28 (1H,d,J=5 Hz), 4.12 (1H,dq,J=6.4 Hz,2 Hz), 6.77–6.95 (2H,m), 7.32–7.44 (1H,m); IR ν max$^{neat}$ cm$^{-1}$: 3420, 2980, 1615, 1600, 1500, 1425.

REFERENCE EXAMPLE 5

2-(2-Fluorophenyl)-2-[(1R)-1-(3,4,5,6-tetrahydro-2H-pyran-2-yl)oxyethyl]oxirane (synthesized by the method disclosed in EP0548553A) was converted into [(1R)-1-[(2R)-2-(2-fluorophenyl)-2-oxiranyl]ethyl] 3,5-dinitrobenzoate by the method described in Reference Examples 1 and 2.

Colorless prisms (recrystallized from ethyl acetate)

mp: 183–184° C.; $^1$H-NMR (CDCl$_3$)δ: 1.47 (3H,dd,J=6.6 Hz,1.6 Hz), 3.03 (1H,d,J=4.7 Hz), 3,23 (1H,d,J=4.7 Hz), 5.35 (1H,q,J=6.6 Hz), 7.09–7.59 (4H,m), 9.13 (2H,d,J=2.2 Hz), 9.23 (1H,t,J=2.2 Hz); [α]$^{23}_D$ −24.7° C. (c=1.0, in CHCl$_3$); Elemental analysis for C$_{17}$H$_{13}$FN$_2$O$_7$; Calcd (%): C,54.26; H,3.48; N,7.44. Found (%): C,54.23; H,3.25; N,7.41.

REFERENCE EXAMPLE 6

[(1R)-1-[(2R)-2-(2-Fluorophenyl)-2-oxiranyl]ethyl] 3,5-dinitrobenzoate was converted into (1R)-1-[(2R)-2-(2-fluorophenyl)-2-oxiranyl]ethanol by the method described in Reference Example 3.

Colorless oily substance $^1$H-NMR (CDCl$_3$)δ: 1.17 (3H,dd,J=6.6 Hz,1.0 Hz), 1.78 (1H,d,J=8.2 Hz), 2.81 (1H,d,J=5.3 Hz), 3.32 (1H,d,J=5.3 Hz), 4.09–4.23 (1H,m), 6.99–7.47 (4H,m).

REFERENCE EXAMPLE 7

(1R)-1-[(2R)-2-(2-Fluorophenyl)-2-oxiranyl]ethanol was converted into (1S)-1-[(2R)-2-(2-fluorophenyl)-2-oxiranyl]-ethanol by the method described in Reference Example 4.

Colorless oily substance $^1$H-NMR (CDCl$_3$)δ: 1.21 (3H,d,J=7 Hz), 2.27 (1H,d,J=2 Hz), 2.96 (1H,d,J=5 Hz), 3.30 (1H,d,J=5 Hz), 4.16 (1H,dq, J=7 Hz,2 Hz), 7.03–7.44 (4H,m).

REFERENCE EXAMPLE 8

2-(2-Fluorophenyl)-2-[(l1R)-1-(3,4,5,6-tetrahydro-2H-pyran-2-yl)oxyethyl] oxirane (synthesized by the method described in EP0548553A) was converted into (1R)-1-[2-(2-fluorophenyl)-2-oxiranyl]ethanol by the method described in Reference Example 1. To an ice-cooled solution of this compound (34.77 g) in tetrahydrofuran (600 ml) were added triphenylphosphine (127.21 g), 3,5-dinitrobenzoic acid (102.88 g) and diethyl azodicarboxylate (84.47 g). The mixture was stirred at room temperature for 7 hours under an argon atmosphere, and then ethyl acetate (600 ml), diisopropyl ether (100 ml) and water (800 ml) were added. The separated aqueous layer was extracted with ethyl acetate (600 ml, 400 ml). The organic layers were combined, washed with water and a saturated aqueous solution of sodium chloride successively, dried over anhydrous magnesium sulfate and concentrated. The residue was purified by silica gel chromatography (eluent: hexane/ethyl acetate=5/1) and recrystallized from ethyl acetate to give [(1S)-1-[(2R)-2-(2-fluorophenyl)-2-oxiranyl]ethyl] 3,5-dinitrobenzoate (23.15 g) as colorless needles.

$^1$H-NMR (CDCl$_3$)δ: 1.47 (3H,d,J=7 Hz), 2.97 (1H,d,J=5 Hz), 3.29 (1H,d,J=5 Hz), 5.43 (1H,q,J=7 Hz), 7.02–7.56 (4H,m), 9.06 (2H,d,J=2 Hz), 9.21 (1H,t,J=2 Hz).

This compound (22.91 g) was dissolved in methanol (700 ml), to which an aqueous solution of 1N-sodium hydroxide (146.5 ml) was added at ice-bath temperature. The mixture was stirred at room temperature for 1 hour. After 1 N-hydrochloric acid (85.5 ml) was added thereto, the solvent was distilled off under reduced pressure. To the residue were added ethyl acetate (500 ml) and water (500 ml). The separated organic layer was washed with water and a saturated aqueous solution of sodium chloride successively, dried over anhydrous magnesium sulfate and concentrated. The residue was purified by silica gel chromatography (eluent: hexane/ethyl acetate=3/1) to give (1S)-1-[(2R)-2-(2-fluorophenyl)-2-oxiranyl]ethanol (10.76 g) as a colorless oily substance. The product was identical with the compound obtained in Reference Example 7.

REFERENCE EXAMPLE 9

A mixture of 4-fluoronitrobenzene (3.1 g), 4-[4-(2,2,3,3-tetrafluoropropoxy)phenyl]-3(2H,4H)-1,2,4-triazolone (5.8 g), potassium carbonate (13.8 g) and N,N-dimethylformamide (60 ml) was stirred at 80° C. for 2 hours. The resultant was cooled and poured into water (500 ml). The mixture was neutralized with hydrochloric acid and the precipitated crystals were collected by filtration. The crystals thus obtained were dissolved in ethyl acetate (300 ml) and dried over anhydrous magnesium sulfate. After filtration, the filtrate was concentrated under reduced pressure. The residue was crystallized from a mixture of ethyl acetate and diisopropyl ether to give 2-(4-nitrophenyl)-4-[4-(2,2,3,3-tetrafluoropropoxy)phenyl]-3(2H,4H)-1,2,4-triazolone (5.5 g, 67%) as yellow crystalline powders.

mp: 161–162° C.

REFERENCE EXAMPLES 10 TO 14

The compounds shown in Table 1 as below were obtained the same manner as in Reference Example 9.

mp: 205–206° C.; 1H-NMR (CDCl$_3$)δ: 7.92 (1H,d,J=1.4 Hz), 8.00 (2H,dt,J=9 Hz,J=2.4 Hz), 8.13 (1H,d,J=1.4 Hz), 8.44 (2H,dt,J=9 Hz,J=2.4 Hz).

REFERENCE EXAMPLE 16

2-(4—Nitrophenyl)-4-[4-(2,2,3,3-tetrafluoropropoxy)-phenyl]-3(2H,4H)-1,2,4-triazolone (5.5 g) and 10% palladium-carbon (50% wet, 0.5 g) were added to methanol (200 ml). The mixture was subjected to catalytic hydrogenation at ordinary temperature under ordinary pressure.

TABLE 1

O$_2$N—⟨phenyl⟩—Az

| Reference Example No. | Az | yield (%) | mp. (° C.) |
|---|---|---|---|
| 10 | [imidazolone]—N⟨phenyl⟩—OCH$_2$CF$_2$CF$_2$H | 75 | 117–118 |
| 11 | [imidazolone]—N⟨phenyl⟩—OCF$_2$CF$_2$H | 70 | 143–145 |
| 12 | [triazolone]—N—CH$_2$CF$_3$ | 45 | 143–145 |
| 13 | [1,2,4-triazole] | 83 | 198–199 |
| 14 | [triazolone]—N—CH$_2$CF$_2$CF$_2$H | 41 | 141–143 |

REFERENCE EXAMPLE 15

4-Fluoronitrobenzene (21 g) was reacted with 1H-1,2,3-triazole (12.4 g) in the same manner as in Reference Example 9. The resultant was cooled and poured into water. The precipitated crystals were collected by filtration and purified by silica gel chromatography (eluent: dichloromethane to dichloromethane/acetone=8/1). The first eluted fraction was recrystallized from dichloromethane-diisopropyl ether to give 2-(4-nitrophenyl)-2H-1,2,3-triazole (18.8 g) as pale yellow prisms.

mp: 183–184° C.; $^1$H-NMR (CDCl$_3$)δ: 7.90 (2H,s), 8.28 (2H,dt,J=9.4 Hz,J=2.4 Hz), 8.38 (2H,dt,J=9.4 Hz,J=2.4 Hz).

Further, the second eluated fraction was recrystallized from dichloromethane-diisopropyl ether to give 1-(4-nitrophenyl)-1H-1,2,3-triazole (6.02 g) as pale yellow prisms.

When hydrogen absoption stopped, dichloromethane (200 ml) was added thereto and the catalyst was removed by filtration. The catalyst was washed with dichloroethane (50 ml). The washings and the filtrate were combined and distilled under reduced pressure to give 2-(4-aminophenyl)-4-[4-(2,2,3,3-tetrafluoropropoxy)phenyl]-3(2H,4H)-1,2,4-triazolone (4.6 g, 90%) as a white solid. This compound was used for next process without purification.

REFERENCE EXAMPLES 17 TO 21

The compounds shown in Table 2 as below were obtained in the same manner as in Reference Example 16.

TABLE 2

$H_2N-\text{C}_6H_4-Az$

| Reference Example No. | Az | yield (%) |
|---|---|---|
| 17 | (triazolone with CH$_2$CF$_3$) | 97 |
| 18 | (1,2,4-triazol-1-yl) | 94 |
| 19 | (1,2,3-triazol-1-yl) | 96 |
| 20 | (pyrazol-1-yl) | 100 |
| 21 | (triazolone with CH$_2$CF$_2$CF$_2$H) | 95 |

REFERENCE EXAMPLE 22

Ferric chloride (0.2 g) and activated carbon (2.0 g) were added to a solution of 1-(4-nitrophenyl)-3-[4-(2,2,3,3-tetrafluoropropoxy)phenyl]-2(1H,3H)-imidazolone (20.5 g) in methanol-tetrahydrofran (75 ml:75 ml), to which hydrazine hydrate (8.0 ml) was added dropwise over the period of 10 minutes. After the mixture was refluxed with stirring for 14 hours, ferric chloride (0.2 g), activated carbon (2.0 g) and hydrazine hydrate (8.0 ml) were added thereto and the reaction mixture was refluxed with stirring for further 6 hours. The activated carbon was filtered off and washed with methanol (100 ml). The filtrate and the washing were combined and distilled off under reduced pressure. The residue thus obtained was dissolved in ethyl acetate (700 ml). The ethyl acetate layer was washed with water (200 ml×4), dried over anhydrous magnesium sulfate and distilled off under reduced pressure to give 1-(4-aminophenyl)-3-[4-(2,2,3,3-tetrafluoropropoxy)phenyl]-2(1H,3H)-imidazolone (18.1 g, 95%) as a pale yellow powder.

mp: 178–179° C.; Elemental analysis for $C_{18}H_{15}F_4N_3O_2$; Calcd (%): C,56.70; H,3.96; N,11.02. Found (%): C,56.58; H,3.93; N,11.21.

REFERENCE EXAMPLE 23

In the same manner as in Reference Example 22, starting from 1-(4-nitrophenyl)-3-[4-(1,1,2,2-tetrafluoroethoxy)phenyl]-2(1H,3H)-imidazolone, 1-(4-aminophenyl)-3-[4-(1,1,2,2-tetrafluoroethoxy)phenyl]-2(1H,3H)-imidazolone was obtained.

mp: 150–151° C.; Elemental analysis for $C_{17}H_{13}F_4N_3O_2$; Calcd (%): C,55.59; H,3.57; N,11.44. Found (%): C,55.74; H,3.40; N,11.49.

REFERENCE EXAMPLE 24

2-(4-Aminophenyl)-4-[4-(2,2,3,3-tetrafluoropropoxy)phenyl]-3(2H,4H)-1,2,4-triazolone (4.6 g) and pyridine (1.43 g) were dissolved in ethyl acetate (200 ml). To the resultant was added dropwise at room temperature a solution of phenyl chlorocarbonate (2.83 g) in ethyl acetate (20 ml). After the addition was completed, the reaction solution was stirred at room temperature for 2 hours. Water (200 ml), ethyl acetate (600 ml) and tetrahydrofuran (300 ml) were added thereto. The separated organic layer was washed with 5% phosphoric acid (200 ml×2) and water (200 ml) successively, dried over anhydrous magnesium sulfate and filtrated. The filtrate was concentrated to about 50 ml and the precipitated crystals were collected by filtration. The crystals thus obtained were washed with diethyl ether and dried to give phenyl 4-[5-oxo-4-[4-(2,2,3,3-tetrafluoropropoxy)phenyl]-1H,4H-1,2,4-triazol-1-yl]phenylcarbamate (5.6 g, 93%) as colorless scaly crystals.

mp: 204–206° C.; Elemental analysis for $C_{24}H_{18}F_4N_4O_4$; Calcd (%): C,57.37; H,3.61; N,11.15. Found (%): C,57.50; H,3.67; N,11.13.

REFERENCE EXAMPLES 25 TO 31

The compounds shown in Table 3 as below were obtained same manner as in Reference Example 24.

TABLE 3

$C_6H_5-OC(O)NH-C_6H_4-Az$

| Reference Example No. | Az | yield (%) | mp. (° C.) |
|---|---|---|---|
| 25 | (imidazolone with OCH$_2$CF$_2$CF$_2$H phenyl) | 89 | 243–244 |

TABLE 3-continued

Structure: Ph-O-C(=O)-NH-C6H4-Az

| Reference Example No. | Az | yield (%) | mp. (° C.) |
|---|---|---|---|
| 26 | 3-methyl-2-oxo-2,3-dihydro-1H-imidazol-1-yl substituted with -OCF₂CF₂H on phenyl | 95 | 208–211 |
| 27 | 2-methyl-5-oxo-4-(2,2,2-trifluoroethyl)-2,5-dihydro-1H-1,2,4-triazol-1-yl (N–CH₂CF₃) | 87 | 183–184 |
| 28 | 1-methyl-1H-1,2,4-triazol-? | 90 | 157–160 |
| 29 | 1-methyl-1H-1,2,3-triazol-? | 96 | 195–200 |
| 30 | 2-methyl-2H-1,2,3-triazol-? | 89 | 143–144 |
| 31 | 2-methyl-5-oxo-4-(2,2,3,3-tetrafluoropropyl)-2,5-dihydro-1H-1,2,4-triazol-1-yl (N–CH₂CF₂CF₂H) | 84 | 173–175 |

REFERENCE EXAMPLE 32

Phenyl 4-[5-oxo-4-[4-(2,2,3,3-tetrafluoropropoxy)phenyl]-1H,4H-1,2,4-triazol-1-yl]phenylcarbamate (5.6 g) was added to a mixture of ethanol (100 ml) and tetrahydrofuran (100 ml). To the resulting mixture was added hydrazine hydrate (3 g) with stirring. The resultant was stirred at 80° C. for 2 hours and concentrated under reduce pressure to about 20 ml. After water (100 ml) was added, the precipitated crystals were collected by filtration, washed with ethanol and dried under reduced pressure to give 4-[4-[5-oxo-4-[4-(2,2,3,3-tetrafluoropropoxy)phenyl]-1H, 4H-1,2,4-triazol-1-yl]phenyl]semicarbazide (4.8 g, 98%) as colorless prisms.

mp: >350° C. Elemental analysis for $C_{18}H_{16}F_4N_6O_3$; Calcd (%): C,49.10; H,3.66; N,19.08. Found (%): C,48.95; H,3.72; N,19.20.

REFERENCE EXAMPLES 33 TO 39

The compounds shown in Table 4 as below were obtained in the same manner as in Reference Example 32.

and washed with water (100 ml). The crystals were dried and dissolved in a mixture of tetrahydrofuran (300 ml) and ethyl acetate (600 ml) with warming. The solution thus obtained was dried over anhydrous magnesium sulfate, filtrated and concentrated under reduced pressure. Ethyl acetate (50 ml) was added to the residue and the precipitated crystals were collected by filtration and recrystallized from tetrahydrofuran to give 4-[4-[5-oxo-4-[4-(2,2,3,3-tetrafluoropropoxy)-phenyl]-1H,4H-1,2,4-triazol-1-yl]phenyl]-3(2H,4H)-1,2,4-triazolone (2.4 g, 49%) as a white crystalline powder.

TABLE 4

H₂NNHCNH—⟨phenyl⟩—Az (O double bond on C)

| Reference Example No. | Az | yield (%) | mp. (° C.) |
|---|---|---|---|
| 33 | imidazolone-OCH₂CF₂CF₂H | 95 | >280 |
| 34 | imidazolone-OCF₂CF₂H | 92 | >250 |
| 35 | triazolone-CH₂CF₃ | 90 | 275–280 |
| 36 | 1,2,4-triazole | 95 | 228–232 |
| 37 | 1,2,3-triazole | 98 | 225–234 |
| 38 | 1,2,3-triazole isomer | 96 | 275–277 |
| 39 | triazolone-CH₂CF₂CF₂H | 95 | 265–274 |

REFERENCE EXAMPLE 40

4-[4-[5-Oxo-4-[4-(2,2,3,3-tetrafluoropropoxy)phenyl]-1H,4H-1,2,4-triazol-1-yl]phenyl]semicarbazide (4.75 g) was added to N,N-dimethylformamide (60 ml). To the mixture were added acetic acid (4 g) and formamidine acetate (6 g), and the resulting mixture was stirred at room temperature for 3 hours and then at 80° C. for 1.5 hours. After cooling, the reaction solution was diluted with water (30 ml). The precipitated crystals were collected by filtration mp: 297–298° C.; Elemental analysis for $C_{19}H_{14}F_4N_6O_3$; Calcd (%): C,50.67; H,3.13; N,18.66; Found (%): C,50.49; H,3.20; N,18.50.

REFERENCE EXAMPLES 41 TO 47

The compounds shown in Table 5 as below were obtained in the same manner as in Reference Example 40.

TABLE 5

[Structure: triazolone-phenyl-Az core with HN-N=N ring, C=O, attached to phenyl-Az]

| Reference Example No. | Az | yield (%) | mp. (°) |
|---|---|---|---|
| 41 | [N-methyl imidazolidinone linked to phenyl-OCH₂CF₂CF₂H] | 52 | >260 |
| 42 | [N-methyl imidazolidinone linked to phenyl-OCF₂CF₂H] | 49 | >260 |
| 43 | [1-methyl-4-(CH₂CF₃)-1,2,4-triazol-5(4H)-one] | 71 | >300 |
| 44 | [1-methyl-1,2,4-triazole] | 40 | >300 |
| 45 | [1-methyl-1,2,3-triazole] | 58 | >300 |
| 46 | [2-methyl-1,2,3-triazole] | 54 | 281–283 |
| 47 | [1-methyl-4-(CH₂CF₂CF₂H)-1,2,4-triazol-5(4H)-one] | 52 | 246–248 |

REFERENCE EXAMPLE 48

A mixture of phenyl 4-(1H-1,2,4-triazol-1-yl) phenylcarbamate (13 g), 2,2-diethoxyethyl amine (7.4 g) and pyridine (3.67 g) was heated at 50° C. for 3 hours. The resultant was cooled and the precipitated crystals were washed with a mixture of diisopropyl ether and petroleum ether (1:1, 100 ml×2) to give 1-(2,2-diethoxyethyl)-3-[4-(1H-1,2,4-triazol-1-yl)phenyl]urea (14.5 g) as a colorless crystalline powder.

mp: 139–140° C.; $^{1}$H-NMR (CDCl$_3$)δ: 1.25 (6H,t,J=7.2 Hz), 3.43 (2H,t,J=5 Hz), 3.52–3.85 (4H,m), 4.57 (1H,t,J=5 Hz), 5.08–5.18 (1H,m), 7.16 (1H,br), 7.49 (2H,d,J=9.4 Hz), 7.57 (2H,d,J=9.4 Hz), 8.08 (1H,s), 8.48 (1H,s).

REFERENCE EXAMPLES 49 TO 50

The compounds shown in Table 6 as below were obtained in the same manner as in Reference Example 48.

TABLE 6

[Structure: (CH₃CH₂O)₂CHCH₂NHC(=O)NH-phenyl-Az]

| Reference Example No. | Az | yield (%) | mp. (° C.) |
|---|---|---|---|
| 49 | [1-methyl-1,2,3-triazole] | 95 | 194–196 |

TABLE 6-continued

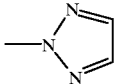

| Reference Example No. | Az | yield (%) | mp. (° C.) |
|---|---|---|---|
| 50 | (triazole) | 84 | 175–176 |

REFERENCE EXAMPLE 51

1-(2,2-Diethoxyethyl)-3-[4-(1H-1,2,4-triazol-1-yl) phenyl]urea (14.5 g) was dissolved in a mixture of methanol (214 ml) and water (85 ml), to which diluted hydrochloric acid (0.48 M, 104 ml) was added dropwise. After the reaction solution was stirred at room temperature for 14 hours, the precipitated crystals were collected by filtration to give 1-[4-(1H-1,2,4-triazol-1-yl)phenyl]-2-(1H,3H)-imidazolone (8.0 g) as a colorless crystalline powder. The filtrate was concentrated under reduced pressure to about 200 ml and the precipitated crystals were collected by filtration to give an additional amount (1.08 g) of the product.

mp: 294–296° C.

REFERENCE EXAMPLES 52 TO 53

The compound shown in Table 7 as below were obtained in the same manner as in Reference Example 51.

TABLE 7

| Reference Example No. | Az | yield (%) | mp. (° C.) |
|---|---|---|---|
| 52 | (triazole) | 86 | 255–251 (decomposition) |
| 53 | (triazole) | 85 | >300 |

REFERENCE EXAMPLE 54

To a solution of (1S)-1-[(2R)-2-(2,4-difluorophenyl)-2-oxiranyl]ethanol (1.0 g) in dichloromethane (14 ml) was added diisopropylethylamine (0.96 ml) at −78° C. in a nitrogen atmosphere, to which trifluoromethanesulfonic anhydride (0.93 ml) was added dropwise over the period of 5 minutes. After the reaction solution was stirred at −78° C. for 20 minutes and then at −25° C. for 25 minutes, the reaction solution was concentrated at −10° C. to about 10 ml. The concentrated solution was subjected to flash column chromatography using silica gel and eluted with dichloromethanehexane (1:1). The desired fraction was concentrated to about 10 ml, and the residue was added at −14° C. to a solution prepared from 4-[4-[5-oxo-4-[4-(2,2,3,3-tetrafluoropropoxy)phenyl]-1H,4H-1,2,4-triazol-1-yl]phenyl]-3(2H,4H)-1,2,4-triazolone (2.1 g), dimethylformamide (40 ml), dimethyl sulfoxide (50 ml) and sodium hydride (60% in oil: 180 mg). The resulting mixture was stirred at −14° C. for 20 minutes and then at −5° C. for 20 minutes. The reaction solution was diluted with water (500 ml) and extracted with dichloromethane (300 ml×2). The dichloromethane layer was washed with water (200 ml×2) and a saturated aqueous solution of sodium chloride successively, dried over anhydrous magnesium sulfate and distilled off under reduced pressure to give a colorless powder. The product was purified by silica gel chromatography (eluent: hexane/ethyl acetate=1/1 to 1/2) and crystallized from ethyl acetatehexane to give 2-[(1R,2S)-2-(2,4-difluorophenyl)-2,3-epoxy-1-methylpropyl]-4-[4-[5-oxo-4-[4-(2,2,3,3-tetrafluoropropoxy)phenyl]-1H-1,2,4-triazol-1-yl]phenyl]-3(2H,4H)-1,2,4-triazolone (0.29 g) as colorless crystalline powders.

mp: 181–183° C.; Elemental analysis for $C_{29}H_{22}F_6N_6O_4$; Calcd (%): C,55.07; H,3.51; N,13.29. Found (%): C,55.12; H,3.34; N,13.24.

REFERENCE EXAMPLES 55 TO 63

The compounds shown in Table 8 as below were obtained in the same manner as in Reference Example 40.

TABLE 8

| Reference Example No. | n | Az | mp. (° C.) |
|---|---|---|---|
| 55 | 1 | (triazole) | 249–250 |
| 56 | 0 | (pyrazole) | 269–270 |
| 57 | 1 | (triazole) | 201–205 |
| 58 | 0 | (imidazole) | 284–286 |
| 59 | 0 | (triazole) | 245–248 |
| 60 | 1 | (triazole) | 250–252 |

TABLE 8-continued

Structure: HN-N=N ring (triazolone) with N-phenyl-(CH$_2$)$_n$-Az

| Reference Example No. | n | Az | mp. (° C.) |
|---|---|---|---|
| 61 | 0 | 2-methyl-thiazol-4-yl (with CH$_3$) | 282–284 |
| 62 | 0 | 2-methyl-oxazol-4-yl (with CH$_3$) | 280–283 |
| 63 | 0 | 1H-tetrazol-1-yl | 243–248 |

REFERENCE EXAMPLES 64 TO 72

The compounds shown in Table 9 as below were obtained in the same manner as in Reference Example 51.

TABLE 9

Structure: HN-imidazol-2-one with N-phenyl-(CH$_2$)$_n$-Az

| Reference Example No. | n | Az | mp. (° C.) |
|---|---|---|---|
| 64 | 0 | pyrazol-1-yl | 239–240 |
| 65 | 1 | 1,2,4-triazol-1-yl | 170–171 |
| 66 | 1 | 1,2,4-triazol-1-yl (isomer) | 190–191 |
| 67 | 0 | imidazol-1-yl | 210–211 |
| 68 | 0 | 1,2,4-triazol-1-yl | 235–240 |
| 69 | 1 | 1,2,3-triazol-1-yl | 213–215 |
| 70 | 0 | 2-methyl-thiazol-4-yl (with CH$_3$) | 206–208 |
| 71 | 0 | 2-methyl-oxazol-4-yl (with CH$_3$) | 216–218 |
| 72 | 0 | 1H-tetrazol-1-yl | 251–255 |

REFERENCE EXAMPLE 73

1-[4-(1H-1-Tetrazolyl)phenyl]-2(1H,3H)-imidazolone (5.0 g) was dissolved in acetic acid (500 ml) and 10% palladium-carbon (50% wet, 5.0 g) was added. The resulting mixture was stirred at 40° C. for 4 hours under a hydrogen atmosphere. The catalyst was filtered and washed with acetic acid. The filtrate and the washings were combined and distilled off under reduced pressure. The residue was crystallized from ethanol to give 1-[4-(1H-1-tetrazolyl)phenyl]-2-imidazolidi-none (4.1 g) as colorless crystals.

mp: 237–240° C. (dec.); $^1$H-NMR (d$_6$-DMSO)δ: 3.45 (2H,t,J=7 Hz), 3.93 (2H,t,J=7 Hz), 7.20 (1H,s), 7.82 (4H,s), 10.02 (1H,s); Elemental analysis for C$_{10}$H$_{10}$N$_6$O; Calcd (%): C,52.17; H,4.38; N,36.50. Found (%): C,51.99; H,4.33; N,36.41.

REFERENCE EXAMPLE 74

Diisopropylethylamine (1.15 ml) was added to a solution of (1S)-1-[(2R)-2-(2,4-difluorophenyl)-2-oxiranyl]ethanol (1.20 g) in dichloromethane (26 ml) at −78° C. under a nitrogen atmosphere, to which trifluoromethanesulfonic anhydride (1.10 ml) was added dropwise over the period of 5 minutes. The mixture was stirred at −78° C. for 20 minutes and then at −30° C. for 15 minutes. After addition of hexane (26 ml), the mixture was subjected to flash column chromatography using silica gel and eluted with dichloromethane-hexane (1:1). The desired fraction was concentrated to about 20 ml, and the residue was added to a solution prepared from 1-[4-(1H-1-tetrazolyl)phenyl]-2 (1H,3H)-imidazolone (940 mg), dimethylformamide (20 ml), dimethyl sulfoxide (10 ml), tetrahydrofuran (10 ml) and sodium hydride (72% in oil: 126 mg) at −30° C. The resulting mixture was stirred for 20 minutes at −30° C. and then for 40 minutes at ice-bath temperature. Water (100 ml) was added and the mixture was extracted with ethyl acetate (150 ml). The ethyl acetate layer was washed with water (100 ml×2) and a saturated aqueous solution of sodium chloride successively, dried over anhydrous magnesium sulfate and distilled off under reduced pressure to give a colorless powder. The product was purified by silica gel chromatography (eluent: hexane/ethyl acetate=1/3) to give 1-[(1R,2S)-2-(2,4-difluorophenyl)-2,3-epoxy-1-methylpropyl]-3-[4-(1H-1-tetrazolyl)phenyl]-2(1H,3H)-imidazolone (0.13 g) and (2R)-2-(2,4-difluorophenyl)-2-[(1R)-1-[1-[4-(1H-1-tetrazolyl)phenyl]-2-imidazolyl]oxylethyl]oxirane (0.05 g).

1-[(1R,2S)-2-(2,4-Difluorophenyl)-2,3-epoxy-1-methylpropyl]-3-[4-(1H-1-tetrazolyl)phenyl]-2(1H,3H)-imidazolone: colorless crystalline powder.

mp: 205–207° C.; $^1$H-NMR (CDCl$_3$)δ: 1.39(3H,d,J=7 Hz), 2.73 (1H,d,J=5 Hz), 2.83 (1H,d,J=5 Hz), 5.09 (1H,q, J=7 Hz), 6.52 (1H,d,J=3 Hz), 6.66 (1H,d,J=3 Hz), 6.81–6.96 (2H,m), 7.36–7.48 (1H,m), 7.78 (2H,d,J=9 Hz), 7.94 (2H, d,J=9 Hz), 9.02 (1H,s); SIMS (MH$^+$): 411.

REFERENCE EXAMPLE 75

Diisopropylethylamine (1.27 ml) was added to a solution of (1S)-1-[(2R)-2-(2-fluorophenyl)-2-oxiranyl]ethanol (1.21 g) in dichloromethane (25 ml) at −78° C. under a nitrogen atmosphere, to which trifluoromethanesulfonic anhydride (1.22 ml) was added dropwise over a period of 5 minutes. The reaction solution was stirred at −78° C. for 15 minutes and then at −30° C. for 15 minutes. The resultant was diluted with hexane (25 ml), subjected to flash column chromatography using silica gel and eluted with dichloromethane-hexane (1:1). The desired fraction was concentrated to about 20 ml, and the residue was added to a solution prepared from 1-[4-(1H-1-tetrazolyl)phenyl]-2(1H,3H)-imidazolone (1.14 g), 1-methyl-2-pyrrolidone (30 ml) and 72% sodium hydride in oil (150 mg) at −30° C. The reaction solution was stirred at −30° C. for 15 minutes and then at −10° C. for 15 minutes. Water (100 ml) was added and the mixture was extracted with ethyl acetate (150 ml). The ethyl acetate layer was washed with water (100 ml) and a saturated aqueous solution of sodium chloride successively, dried over anhydrous magnesium sulfate and distilled off under reduced pressure to give a colorless powder. The product was purified by silica gelchromatography (eluent: hexane/ethyl acetate=1/3) to give 1-[(1R,2S)-2-(2-fluorophenyl)-2,3-epoxy-1-methylpropyl]-3-[4-(1H-1-tetrazolyl)phenyl]-2(1H,3H)-imidazolone (0.39 g) and (2R)-2-(2-fluorophenyl)-2-[(1R)-1-[1-[4-(1H-1-tetrazolyl)phenyl]-2-imidazolyloxy]ethyl]oxirane (0.18 g).

1-[(1R,2S)-2-(2-Fluorophenyl)-2,3-epoxy-1-methylpropyl]-3-[4-(1H-1-tetrazolyl)phenyl]-2(1H,3H)-imidazolone:
colorless crystalline powder.

$^1$H-NMR (CDCl$_3$)δ: 1.39(3H,d,J=7 Hz), 2.76 (1H,d,J=5 Hz), 2.84 (1H,d,J=5 Hz), 5.15 (1H,q,J=7 Hz), 6.55 (1H,d, J=3 Hz), 6.67 (1H,d,J=3 Hz), 7.06–7.49 (4H,m), 7.79 (2H, d,J=9 Hz), 7.96 (2H,d,J=9 Hz), 9.04 (1H,s)

REFERENCE EXAMPLE 76

A mixture of (S)-ethyl lactate (75 g) and morpholine (164 g) was heated at 80° C. for 64 hours. The reaction solution was concentrated and the residue was subjected to silica gel chromatography (eluent: hexane/ethyl acetate=4/1 to ethyl acetate) to give 4-[(S)-2-hydroxypropionyl]-morpholine (69.4 g) as a pale yellow oily substance. p-Toluenesulfonic acid monohydrate (0.82 g) was added to a solution of 4-[(S)-2-hydroxypropionyl]morpholine (69.4 g) in dichloromethane (300 ml), to which 3,4-dihydro-2H-pyran (40.3 g) was added dropwise at ice-bath temperature. The reaction solution was stirred at 0° C. for 30 minutes and washed with a 5% aqueous solution of sodium bicarbonate. After the organic layer was dried over anhydrous magnesium sulfate and concentrated, the residue was subjected to silica gel chromatography (eluent: hexane/ethyl acetate=8/1 to ethyl acetate) to give 4-[(2S)-2-(3,4,5,6-tetrahydro-2H-pyran-2-yloxy)propionyl]morpholine (89.1 g) as a pale yellow oily substance.

1-Bromo-2-fluorobenzene (15 g) and 4-[(2S)-2-(3,4,5,6-tetrahydro-2H-pyran-2-yloxy)propionyl]morpholine (40 g) were dissolved in tetrahydrofuran (200 ml), to which magnesium (turnings: 4.4 g) was added. The mixture was stirred vigorously. The reaction flask was cooled when the temperature of the reaction solution reached to 35° C., and 1-bromo-2-fluorobenzene (16.7 g) was added thereto over the period of 10 minutes while the temperature of the reaction solution was kept at 35 to 37° C. After the reaction solution was stirred at 30 to 35° C. for 2 hours, it was cooled in an icebath. A saturated aqueous solution of ammonium chloride (100 ml) was added thereto and the mixture was extracted with ethyl acetate (200 ml×2,100 ml). The extract was washed with water and a saturated aqueous solution of sodium chloride successively, dried over anhydrous magnesium sulfate, and distilled under reduced pressure to remove the solvent. The residue was subjected to silica gel chromatography (eluent: hexane/ethyl acetate=10/1 to 5/1) to give (2S)-2'-fluoro-2-(3,4,5,6-tetrahydro-2H-pyran-2-yloxy)-propiophenone (22.4 g) as a pale yellow oily substance.

(2S)-2'-Fluoro-2-(3,4,5,6-tetrahydro-2H-pyran- 2-yloxy) propiophenone (25 g) was dissolved in ethanol (200 ml), to which pyridinium p-toluenesulfonate (1.28 g) was added. The reaction solution was stirred at 55° C. for 2.5 hours and then concentrated. The residue was subjected to silica gel chromatography (eluent: hexane/ethyl acetate=9/1 to 5/1) to give (2S)-2'-fluoro-2-hydroxypropiophenone (16.4 g) as a colorless oily substance.

IR(neat): 1690 (C=0) cm$^{-1}$; $^1$H-NMR (CDCl$_3$)δ: 1.41(3H, dd,J=7 Hz,J=1.4 Hz), 3.78 (1H,d,J=6 Hz), 4.98–5.15 (1H, m), 7.12–7.36 (2H,m), 7.54–7.68 (1H,m), 7.90–8.00 (1H,m)

REFERENCE EXAMPLE 77

(2S)-2',4'-Difluoro-2-hydroxypropiophenone (synthesized by the method disclosed in Japanese Unexamined Patent Publication No. Hei 5(1993)-230038: 26.01 g) was dissolved in dichloromethane (300 ml), to which diisopropylethylamine (19.90 g) was added at −60° C. under a nitrogen atmosphere, and then trifluoromethanesulfonic anhydride (25.90 ml) was added thereto dropwise over the period of 20 minutes. After the reaction temperature was gradually raised to −30° C., the reaction solution was further stirred for 30 minutes. The reaction solution was purified by silica gel chromatography (silica gel 400 g, eluent: dichloromethane/hexane=1/1) to give (2S)-2',4'-difluoro-2-trifluoromethanesulfonyloxypropiophenone (39.21 g) as a pale yellow oily substance.

$^1$H-NMR (CDCl$_3$)δ: 1.73(3H,dd,J=7.0 Hz,1.6 Hz), 5.93 (1H,q,J=7.0Hz), 6.90–7.12 (2H,m), 8.03 (1H,dt,J=6.4 Hz,8.6 Hz); [α]$_D^{23}$+29.2° (c=1.12, in MeOH);

REFERENCE EXAMPLE 78

(2S)-2'-Fluoro-2-hydroxypropiophenone (synthesized by the method disclosed in Reference Example 76: 3.36 g) was dissolved in dichloromethane (30 ml). To the resultant was added diisopropylethylamine (4.18 ml) at −60° C. under a nitrogen atmosphere, and then trifluoromethanesulfonic anhydride (4.03 ml) was added dropwise to the mixture over the period of 2 minutes. After the reaction temperature was gradually raised to −25° C., the reaction solution was stirred for 30 minutes. The reaction solution was purified by silica gel chromatography (silica gel 60 g, eluent: dichloromethane/hexane=1/1) to give (2S)-2'-fluoro-2-trifluoromethanesulfonyloxypropiophenone (5.30 g) as a pale yellow oily substance.

$^1$H-NMR (CDCl$_3$)δ: 1.73(3H,dd,J=7 Hz,J=1.6 Hz), 6.49 (1H,q,J=7 Hz), 7.15–7.38 (2H,m), 7.58–7.72 (1H,m), 7.97 (1H,dt,J=1.8 Hz,J=7.6 Hz).

REFERENC EXAMPLE 79

1-[4-(1H-1,2,4-Triazol-1-yl)phenyl]-2(1H,3H)-imidazolone (3.39 g) was dissolved in 1-methyl-2-pyrrolidone (220 ml), to which 72% sodium hydride in oil (528 mg) was added. The mixture was stirred at room temperature for 1 hour. The reaction solution was cooled in an ice-bath and added dropwise over the period of 15 minutes to a solution of (2S)-2'-fluoro-2-trifluoromethanesulfonyloxypropiophenone (4.7 g) in tetrahydrofuran (100 ml) which had been cooled to −20° C. After the addition was complete, the reaction temperature was raised to 10° C. over 30 minutes and the reaction solution was further stirred for 12 hours. The reaction solution was diluted with acetic acid (10 ml) and ethyl acetate (500 ml), washed with water (250 ml×2), 0.5 hydrochloric acid (250 ml×2) and a saturated aqueous solution of sodium chloride (250 ml) successively, dried over anhydrous magnesium sulfate and distilled under reduced pressure to remove the solvent. The residue was purified by silica gel chromatography (silica gel, eluent: hexane/ethyl acetate/acetic acid=1/4/0.06) and recrystallized from diisopropyl ether (25 ml) to give 1-[(1R)-2-(2-fluorophenyl)-2-oxo-1-methylethyl]-3-[4-(1H-1,2,4-triazol-1-yl)phenyl]-2(1H,3H)-imidazolone as a colorless crystalline powder.

$^1$H-NMR (CDCl$_3$)δ: 1.65(3H,d,J=7.2 Hz), 5.82 (1H,q,J=7.2 Hz), 6.64 (1H,d,J=3.2 Hz), 6.70 (1H,d,J=3.2 Hz), 7.14–7.31 (2H,m), 7.53–7.94 (6H,m), 8.11 (1H,s), 8.56 (1H,s)

REFERENCE EXAMPLE 80

1-[4-(1H-1-Tetrazolyl)phenyl]-2(1H,3H)-imidazolone (0.94 g) was dissolved in 1-methyl-2-pyrrolidone (25 ml), to which 72% sodium hydride in oil (0.126 g) was added. The reaction solution was stirred at room temperature for 30 minutes. The resultant was ice-cooled and added dropwise over the period of 10 minutes to a solution of (2S)-2'-fluoro-2-trifluoromethanesulfonyloxypropiophenone (1.57 g) in tetrahydrofuran (25 ml) which had been cooled to −10° C. After the addition was complete, the reaction temperature was raised to 0° C. over 15 minutes and the reaction solution was stirred for 30 minutes. The reaction solution was diluted with acetic acid (3 ml) and ethyl acetate (100 ml), washed with water (50 ml×2), 0.5 N-hydrochloric acid (50 ml×2) and a saturated aqueous solution of sodium chloride (50 ml) successively, dried over anhydrous magnesium sulfate and distilled under reduced pressure to remove the solvent. The residue was purified by silica gel chromatography (eluent: hexane/ethyl acetate/acetic acid=1/3/0.05) and recrystallized from diisopropyl ether (20 ml) to give 1-[(1R)-2-fluorophenyl)-2-oxo-1-methylethyl]-3-[4-(1H-1-tetrazolyl) phenyl]-2(1H,3H)-imidazolone (0.22 g) as a colorless crystalline powder.

mp: 162–164° C.;

$^1$H-NMR (CDCl$_3$)δ: 1.66 (3H,d,J=7.2 Hz), 5.83 (1H,q,J=7.2 Hz), 6.67 (1H,d,J=3.2 Hz), 6.74 (1H,d,J=3.2 Hz), 7.16–7.33 (2H,m), 7.54–7.98 (2H,m), 7.77 (2H,d,J=9 Hz), 7.91 (2H,d,J=9 Hz), 9.03 (1H,s).

REFERENCE EXAMPLE 81

Chloromethylisopropoxydimethylsilane (2.14 g) and magnesium (for Grignard reaction, 313 mg) were added to tetrahydrofuran (15 ml), and the mixture was heated to 60° C. To the mixture was added magnesium in the form of turnings which had been activated by methyl iodide, and then the mixture was stirred in a bath at 60° C. for 3 hours.

The solution of the Grignard reagent thus obtained was added dropwise to a solution of 1-[(1R)-2-(2-fluorophenyl)-2-oxo-1-methylethyl]-3-[4-(1H-1-tetrazolyl)phenyl-2(1H,3H)-imidazolone (1 g) in tetrahydrofuran (150 ml) over the period of 10 minutes at ice-bath temperature, and the mixture was stirred for 30 minutes. A cooled saturated aqueous solution of ammonium chloride (30 ml) and cooled water (100 ml) were added thereto at ice-bath temperature and the mixture was extracted with ethyl acetate (200 ml). The extract was washed with a saturated aqueous solution of sodium chloride, dried over magnesium sulfate and concentrated under reduced pressure. The residue was recrystallized from a mixture of diisopropyl ether and ethyl acetate to give 1-[((R,2S)-2-(2-fluorophenyl)-2-hydroxy-3-(isopropoxydimethylsilyl)-1-methylpropyl]-3-[4-(1H-1-tetrazolyl)phenyl]-2(1H,3H)-imidazolone (637 mg) as a colorless crytalline powder.

$^1$H-NMR (d$_6$-DMSO)δ: −0.30(3H,s), −0.28 (3H,s), 0.99–1.64 (11H,m), 3.83 (1H,quintet,J=6 Hz), 4.81 (1H,q, J=7 Hz), 5.21 (1H,br), 6.93–7.77 (6H,m), 8.05 (2H,d,J=9 Hz), 8.17 (2H,d,J=9 Hz), 10.17 (1H,s).

REFERENCE EXAMPLE 82

1-[(1R,2S)-2-(2-Fluorophenyl)-2-hydroxy-3-(isopropoxy dimethylsilyl)-1-methylpropyl]-3-[4-(1H-1-tetrazolyl) phenyl]-2(1H,3H)-imidazolone (1 g) was dissolved in a mixture of methanol and tetrahydrofuran (1:1, 20 ml), to which an 30% aqueous solution of hydrogen peroxide (2 ml) and sodium bicarbonate (157 mg) were added. The mixture was heated at 50° C. for 4 hours, then cooled and extracted with ethyl acetate (100 ml). The extract was washed with water (30 ml), an aqeous solution of Na$_2$S$_2$O$_3$ (30 ml×2) and a saturated aqueous solution of sodium chloride (30 ml) successively, dried over magnesium sulfate and distilled under reduced pressure to remove the solvent. The residue was purified by silica gel chromatography (eluent: hexane/ethyl acetate=1/4) and recrystallized from diethyl ether (20 ml) to give 1-[(1R,2S)-2-(2-fluorophenyl)-2,3-dihydroxy-1-methyl propyl]-3-[4-(1H-1-tetrazolyl)phenyl]-2(1H,3H)-imidazolone (440 mg) as a colorless crystalline powder.

$^1$H-NMR (CDCl$_3$)δ: 1.17(3H,d,J=7 Hz), 3.52–3.62 (1H, m), 4.05–4.18 (2H,m), 5.01 (1H,q,J=7 Hz), 6.72 (1H,d,J=3.2 Hz), 6.82 (1H,d,J=3.2 Hz), 7.01–7.33 (3H,m), 7.70–7.78 (1H,m), 7.90 (2H,d,J=9 Hz), 7.99 (2H,d,J=9 Hz), 9.55 (1H,s).

REFERENCE EXAMPLE 83

1-[(1R,2S)-2-(2-Fluorophenyl)-2,3-dihydroxy-1-methyl propyl]-3-[4-(1H-1-tetrazolyl)phenyl]-2(1H,3H)-imidazolone (440 mg) was dissolved in a mixture of ethyl acetate and tetrahydrofuran (1:2, 30 ml), to which methanesulfonyl chloride (0.18 g) and triethylamine (0.16 g) were added dropwise at ice-bath temperature. The reaction solution was stirred at 0° C. for 30 minutes and washed with water (15 ml×2) and a saturated aqueous solution of sodium chloride (15 ml) successively. The organic layer was dried over magnesium sulfate and distilled under reduced pressure to remove the solvent. The residue was purified by silica gel chromatography (eluent: hexane/ethyl acetate=1/4) to give 1-[(1R,2S)-2-(2-fluorophenyl)-2-hydroxy-3-methanesulfonyloxy-1-methylpropyl]-3-[4-(1H-1-tetrazolyl)phenyl]-2(1H,3H)-imidazolone (330 mg) as a colorless crystalline powder.

$^1$H-NMR (CDCl$_3$)δ: 1.27(3H,d,J=7 Hz), 2.87 (3H,s), 4.54 (1H,d,J=12 Hz), 4.73–4.88 (2H,m), 6.63 (1H,d,J=3.2 Hz), 6.72 (1H,d,J=3.2 Hz), 7.09–7.39 (3H,m), 7.75–7.94 (1H,m), 7.81 (2H,d,J=9 Hz), 7.93 (2H,d,J=9 Hz), 9.04 (1H,s).

REFERENCE EXAMPLE 84

1-[(1R,2S)-2-(2-Fluorophenyl)-2-hydroxy-3-methanesulfonyloxy-1-methylpropyl]-3-[4-(1H-1-tetrazolyl)phenyl]-2(1H,3H)-imidazolone (100 mg) was dissolved in dimethylformamide (4 ml), to which potassium carbonate (42 mg) was added, and the mixture was heated at 40° C. for 1 hour. The resultant was diluted with ethyl acetate (20 ml) and washed with water (10 ml) and a saturated aqueous solution of sodium chloride (10 ml) successively. The organic layer was dried over magnesium sulfate and distilled under reduced pressure to remove the solvent. The residue was purified by silica gel chromatography (eluent: hexane/ethyl acetate=1/4). The desired fraction was concentrated and the residue was recrystallized from diisopropyl ether to give 1-[(1R,2S)-2-(2-fluorophenyl)-2,3-epoxy-1-methylpropyl]-3-[4-(1H-1-tetrazolyl)phenyl]-2(1H,3H)-imidazolone (58 mg) as a colorless crystalline powder.

$^1$H-NMR (CDCl$_3$)δ: 1.40 (3H,d,J=7 Hz), 2.76 (1H,d,J=5 Hz), 2.84 (1H,d,J=5 Hz), 5.15 (1H,q,J=7 Hz), 6.55 (1H,d,J=3.2 Hz), 6.67 (1H,d,J=3.2 Hz), 7.07–7.48 (4H,m), 7.79 (2H,d,J=9 Hz), 7.95 (2H,d,J=9 Hz), 9.05 (1H,s).

WORKING EXAMPLE 1

60% sodium hydride in oil (108 mg) was dispersed in dimethylformamide (4 ml), to which 1,2,4-triazole (207 mg) was added at ice-bath temperature, and the mixture was stirred at room temperature for 10 minutes. To the resultant was added a solution of 2-[(1R, 2S)-2-(2,4-difluorophenyl)-2,3-epoxy-1-methylpropyl]-4-[4-[5-oxo-4-[4-(2,2,3,3-tetrafluoropropoxy)phenyl]-1H-1,2,4-triazol-1-yl]phenyl]-3 (2H,4H)-1,2,4-triazolone (560 mg) in dimethylformamide (2 ml), and the mixture was heated at 60° C. for 11 hours. After cooling, water (40 ml) and ethyl acetate (40 ml) were added to the mixture. The separated aqueous layer was extracted with ethyl acetate twice. The combined ethyl acetate layers were washed with water and a saturated aqueous solution of sodium chloride successively, dried over anhydrous magnesium sulfate and distilled under reduced pressure to remove the solvent. The residue was purified by silica gel chromatography (eluent: ethyl acetate/hexane= 19/1 to ethyl acetate) and then by reverse phase chromatography (eluent: ethanol/water=4/1) to give 2-[(1R,2R)-2-(2, 4-difluorophenyl)-2-hydroxy-1-methyl-3-(1H-1,2,4-triazol-1-yl)propyl]-4-[4-[5-oxo-4-[4-(2,2,3,3-tetrafluoropropoxy) phenyl]-1H-1,2,4-triazol-1-yl]phenyl]-3(2H,4H)-1,2,4-triazolone (Compound 1; 0.21 g) as a colorless powder.

[α]$^{20}$$_D$–16.9° (c=1.0% in MeOH); Elemental analysis for C$_{31}$H$_{25}$F$_6$N$_9$O$_4$·0.5H$_2$O; Calcd (%): C,52.40; H,3.69; N.17.74. Found (%): C,52.59; H,3.67; N,17.69.

WORKING EXAMPLE 2

(2R,3S)-2-(2,4-Difluorophenyl)-3-methyl-2-(1H-1,2,4-triazol-1-yl)methyloxirane (1.2 g), 4-[4-[2-oxo-3-[4-(2,2,3, 3-tetrafluoropropoxy)phenyl]-1H,3H-imidazol-1-yl] phenyl]-3(2H,4H)-1,2,4-triazolone (2.2 g) and potassium carbonate (powder: 3.5 g) were added to N,N-dimethylformamide (50 ml), and the mixture was heated with stirring at 90° C. for 42 hours. After cooling, the resultant was diluted with ethyl acetate (150 ml) and tetrahydrofuran (50 ml). Ice water (150 ml) was added thereto to separate the ethyl acetate layer. The aqueous layer was extracted with ethyl acetate (100 ml). The ethyl acetate layers were combined and washed with 0.5N-sodium hydroxide (100 ml), 1N-hydrochloric acid (100 ml) and a saturated aqueous solution of sodium chloride (100 ml) successively. The ethyl acetate layer was dried over anhydrous magnesium sulfate and distilled under reduced pressure to remove the solvent. The residue was purified by silica gel chromatography (elute:ethyl acetate/acetone=10/1) and crystallized from tetrahydrofuran-diisopropyl ether to give 2-[(1R,2R)-2-(2,4-difluorophenyl)-2-hydroxy-1-methyl-3-(1H-1,2,4-triazol-1-yl)propyl]-4-[4-[2-oxo-3-[4-(2,2,3,3-tetrafluoropropoxy)-phenyl]-1H,3H-imidazol-1-yl]phenyl]-3(2H,4H)-1,2,4-triazolone (Compound 2; 0.26 g) as a colorless crystalline powder.

mp: 181–183° C.; Elemental analysis for C$_{32}$H$_{26}$F$_6$N$_8$O$_4$; Calcd (%): C,54.86; H,3.74; N.15.99. Found (%): C,54.58; H,3.75; N,15.71. [α]$^{20}$$_D$–18.9° (c=1.0% in MeOH).

WORKING EXAMPLE 3

2-[(1R,2R)-2-(2,4-Difluorophenyl)-2-hydroxy-1-methyl-3-(1H-1,2,4-triazol-1-yl)propyl]-4-[4-[2-oxo-3-[4-(1,1,2,2-tetrafluoroethoxy)phenyl]-1H,3H-imidazol-1-yl] phenyl]-3 (2H,4H)-1,2,4-triazolone (Compound 3) was obtained in the same manner as in Working Example 2,
Colorless crystalline powder
mp: 214–215° C. Elemental analysis for C$_{31}$H$_{24}$F$_6$N$_8$O$_4$; Calcd (%): C,54.23; H,3.52; N,16.32. Found (%): C,54.05; H,3.37; N,16.32. [α]$^{20}$$_D$–19.0° (c=1.0% in MeOH).

WORKING EXAMPLE 4

A mixture of 60% sodium hydride in oil (0.24 g) and dimethyl sulfoxide (60 ml) was stirred at 80° C. for 30 minutes. To the mixture was added 4-[4-[5-oxo-4-(2,2,2-trifluoroethyl)-1H,4H-1,2,4-triazol-1-yl]phenyl]-3(2H,4H)-1,2,4-triazolone (1.94 g), and the mixture was stirred for 5 minutes. To the resultant was added (2R,3S)-2-(2,4-difluorophenyl)-3-methyl-2-(1H-1,2,4-triazol-1-yl) methyloxirane (1.0 g), and the mixture was stirred at 80° C. for 24 hours under an argon atmosphere. The reaction solution was cooled, diluted with ethyl acetate (300 ml) and washed with water (50 ml×2) and a saturated aqueous solution of sodium chloride (50 ml) successively. The organic layer was dried over magnesium sulfate and concentrated under reduced pressure. The residue was purified by silica gel chromatography (eluent: hexane/ethyl acetate= 1/2 to ethyl acetate) to give 2-[(1R,2R)-2-(2,4-difluorophenyl)-2-hydroxy-1-methyl-3-(1H-1,2,4-triazol-1-yl)propyl]-4-[4-[5-oxo-4-[4-(2,2,2-trifluoroethyl)-1H,4H-1, 2,4-triazol-1-yl]phenyl]-3-(2H,4H)-1,2,4-triazolone (Compound 4; 0.46 g) as a pale yellow powder.

$^1$H-NMR (CDCl$_3$)δ: 1.31(3H,d,J=7 Hz), 4.36 (2H,q,J=8.4 Hz), 4.37 (1H,d,J=14 Hz), 5.03 (1H,d,J=14 Hz), 5.10 (1H, q,J=7 Hz), 5.44 (1H,s), 6.75–6.88 (2H,m), 7.48–7.65 (1H, m), 7.67 (2H,d,J=9 Hz), 7.68 (1H,s), 7.69 (1H,s), 7.83 (1H,s), 7.94 (1H,s), 8.16 (2H,d,J=9 Hz).

WORKING EXAMPLE 5

(2R,3S)-2-(2,4-Difluorophenyl)-3-methyl-2-(1H-1,2,4-triazol-1-yl)methyloxirane (1.0 g) was reacted with 4-[4-

(1H-1,2,4-triazol-1-yl)phenyl]-3(2H,4H)-1,2,4-triazolone (0.91 g) in the same manner as in Working Example 4 to give 2-[(1R,2R)-2-(2,4-difluorophenyl)-2-hydroxy-1-methyl-3-(1H-1,2,4-triazol-1-yl)propyl]-4-[4-(1H-1,2,4-triazol-1-yl)phenyl]-3(2H,4H)-1,2,4-triazolone (Compound 5; 0.54 g).
Colorless crystalline powder mp: 182–184° C.; $^1$H-NMR (CDCl$_3$)δ: 1.32(3H,d,J=7 Hz), 4.40 (1H,d,J=14.4 Hz), 5.03 (1H,d,J=14.4 Hz), 5.11 (1H,q,J=7 Hz), 5.41 (1H,s), 6.75–6.90 (2H,m), 7.50–7.65 (1H,m), 7.69 (1H,s), 7.79 (2H,d,J=9 Hz), 7.88 (2H,d,J=9 Hz), 7.92 (1H,s), 7.96 (1H,s), 8.14(1H,s), 8.65 (1H,s); Elemental analysis for C$_{22}$H$_{19}$F$_2$N$_9$O$_2$; Calcd (%): C,55.11; H,3.99; N,26.29. Found (%): C,55.05; H,4.01; N,26.14. IR(KBr): 1714, 1618, 1556, 1527, 1394 cm$^{-1}$.

WORKING EXAMPLE 6

(2R,3S)-2-(2,4-Difluorophenyl)-3-methyl-2-(1H-1,2,4-triazol-1-yl)methyloxirane (1.0 g) was reacted with 4-[4-(1H-1,2,3-triazol-1-yl)phenyl]-3(2H,4H)-1,2,4-triazolone (1.09 g) in the same manner as in Working Example 4 to give 2-[(1R,2R)-2-(2,4-difluorophenyl)-2-hydroxy-1-methyl-3-(1H-1,2,4-triazol-1-yl)propyl]-4-[4-(1H-1,2,3-triazol-1-yl)phenyl]-3(2H,4H)-1,2,4-triazolone (Compound 6; 0.27 g).
Colorless crystalline powder mp: 219–220° C.; $^1$H-NMR (CDCl$_3$)δ: 1.32(3H,d,J=7 Hz), 4.40 (1H,d,J=14.2 Hz), 5.03 (1H,d,J=14.2 Hz), 5.10 (1H,q,J=7 Hz), 5.38 (1H,s), 6.75–6.90 (2H,m), 7.50–7.65 (1H,m), 7.70 (1H,s), 7.82 (2H,d,J=9 Hz), 7.88 (1H,s), 7.90 (1H,s), 7.94 (2H,d,J=9 Hz), 7.94 (1H,s), 8.05 (1H,s); Elemental analysis for C$_{22}$H$_{19}$F$_2$N$_9$O$_2$; Calcd (%): C,55.11; H,3.99; N,26.29. Found (%): C,54.91; H,3.97; N,26.26. IR(KBr): 1700, 1675, 1618, 1556, 1527, 1502 cm$^{-1}$.

WORKING EXAMPLE 7

(2R,3S)-2-(2,4-Difluorophenyl)-3-methyl-2-(1H-1,2,4-triazol-1-yl)methyloxirane (1.0 g) was reacted with 4-[4-(2H-1,2,3-triazol-2-yl)phenyl]-3(2H,4H)-1,2,4-triazolone (1.09 g) in the same manner as in Working Example 4 to give 2-[(1R,2R)-2-(2,4-difluorophenyl)-2-hydroxy-1-methyl-3-(1H-1,2,4-triazol-1-yl)propyl]-4-(4-(2H-1,2,3-triazol- 2-yl)phenyl]-3(2H,4H)-1,2,4-triazolone (Compound 7; 0.65 g).
Pale yellow plates mp: 213–215° C. $^1$H-NMR (CDCl$_3$)δ: 1.32(3H,d,J=7 Hz), 4.38 (1H,d,J=14.2 Hz), 5.04 (1H,d,J=14.2 Hz), 5.11 (1H,q, J=7 Hz), 5.42 (1H,s), 6.75–6.90 (2H,m), 7.50–7.64 (1H,m), 7.69 (1H,s), 7.74 (2H,d,J=9 Hz), 7.85 (2H,s), 7.86 (1H,s), 7.95 (1H,s), 8.25(2H,d,J=9 Hz); Elemental analysis for C$_{22}$H$_{19}$F$_2$N$_9$O$_2$; Calcd (%): C,55.11; H,3.99; N,26.29. Found (%): C,54.97; H,3.96; N,26.29. IR(KBr): 1697, 1623, 1602,1564, 1519, 1510 cm$^{-1}$.

WORKING EXAMPLE 8

2-[(1R,2R)-2-(2,4-Difluorophenyl)-2-hydroxy-1-methyl-3-(1H-1,2,4-triazol-1-yl)propyl3–4-[4-[5-oxo-4-[4-(2,2,3,3-tetrafluoropropyl)-1H,4H-1,2,4-triazol-1-yl]phenyl]-3-(2H,4H)-1,2,4-triazolone (Compound 8) was obtained in the same manner as in Working Example 4.
Pale yellow powder $^1$H-NMR (CDCl$_3$)δ: 1.31(3H,d,J=7 Hz), 4.34 (2H,t,J=14 Hz), 4.37 (1H,d,J=14 Hz), 5.04 (1H,d,J=14 Hz), 5.10 (1H, q,J=7 Hz), 5.46 (1H,s), 5.98 (1H,tt,J=53 Hz,J=2.4 Hz), 6.75–6.90 (2H,m), 7.50–7.65 (1H,m), 7.67 (2H,d,J=9 Hz), 7.68 (1H,s), 7.72 (1H,s), 7.86 (1H,s), 7.96 (1H,s), 8.16 (2H,d,J=9 Hz).

WORKING EXAMPLE 9

(2R,3S)-2-(2,4-Difluorophenyl)-3-methyl-2-(1H-1,2,4-triazol-1-yl)methyloxirane (2.5 g), 1-[4-(1H-1,2,4-triazol-1-yl)phenyl]-2(1H,3H)-imidazolone (2.72 g) and cesium carbonate (powder: 9.7 g) were added to N,N-dimethylformamide (150 ml), and the mixture was heated at 80° C. with stirring for 9.5 hours. After cooling, the reaction mixture was diluted with ethyl acetate (400 ml). Ice water (150 ml) was added thereto to separate the ethyl acetate layer. The aqueous layer was extracted with ethyl acetate (100 ml). The ethyl acetate layers were combined and washed with 0.5N-sodium hydroxide (100 ml), 1N-hydrochloric acid (100 ml×2) and a saturated aqueous solution of sodium chloride (50 ml) successively. The ethyl acetate layer was dried over anhydrous magnesium sulfate and distilled under reduced pressure to remove the solvent. The residue was purified by silica gel chromatography (eluent: ethyl acetate/acetone=2/1) to give 1-[((1R,2R)-2-(2, 4-difluorophenyl)-2-hydroxy-1-methyl-3-(1H-1,2,4-triazol-1-yl)propyl]-3-[4-(1H-1,2,4-triazol-1-yl)phenyl]-2(1H,3H)-imidazolone (Compound 9; 1.03 g) as a pale yellow powder.

$^1$H-NMR (CDCl$_3$)δ: 1.21 (3H,d,J=7 Hz), 4.22 (1H,d,J= 14.2 Hz), 5.01 (1H,q,J=7 Hz), 5.12 (1H,d,J=14.2 Hz), 5.50 (1H,br), 6.72 (1H,d,J=3.2 Hz), 6.73–6.90 (2H,m), 6.83 (1H, d,J=3.2 Hz), 7.40–7.55 (1H,m), 7.75 (1H,s), 7.78 (2H,d,J= 9.4 Hz), 7.86 (1H,s), 7.86 (2H,d,J=9.4 Hz), 8.13 (1H,s), 8.59 (1H,s). IR(KBr): 3400, 3118, 1683, 1616, 1527, 1500 cm$^{-1}$.

WORKING EXAMPLE 10

1-[(1R,2R)-2-(2,4-Difluorophenyl)-2-hydroxy-1-methyl-3-(1H-1,2,4-triazol-1-yl)prepyl]-3-[4-(1H-1,2,4-triazol-1-yl)phenyl]-2(1H,3H)-imidazolone (0.50 g) obtained in Working Example 9 was dissolved in acetic acid (25 ml), to which 10% palladium-carbon (200 mg) was added. The resultant was stirred under a hydrogen atmosphere at room temperature for 3 hours and then at 50° C. for 3 hours. After the catalyst was filtered off, the filtrate was concentrated. The residue was purified by silica gel chromatography (eluent: ethyl acetate/acetone=5/1 to 2/1) and recrystallized from ethyl acetate-diisopropyl ether to give 1-[(1R,2R)-2-(2,4-difluorophenyl)-2-hydroxy-1-methyl-3-(1H-1,2,4-triazol-17 yl)propyl]-3-[4-(1H-1,2,4-triazol-1-yl)phenyl]-2-imidazolidinone (Compound 10; 0.37 g) as a colorless crystalline powder.

$^1$H-NMR (CDCl$_3$)δ: 1.08(3H,d,J=7.2 Hz), 3.68–4.18 (4H, m), 4.52 (1H,d,J=14 Hz), 4.58–4.80 (1H,m), 5.12 (1H,d,J= 14 Hz), 5.38 (1H,br), 6.70–6.86 (2H,m), 7.35–7.50 (1H,m), 7.66 (2H,dt,J=9.4 Hz,J=2.4 Hz), 7.75 (2H,dt,J=9.4 Hz,J=2.4 Hz), 7.77 (1H,s), 7.87 (1H,s), 8.11 (1H,s), 8.53 (1H,s). Elemental analysis for C$_{23}$H$_{22}$F$_2$N$_8$O$_2$; Calcd (%): C,57.50; H,4.62; N,23.32; Found (%): C,57.46; H,4.47; N,23.19. IR(KBr): 3390, 3106, 1677, 1614, 1523, 1484 cm$^{-1}$.

WORKING EXAMPLE 11

To a mixture of 1-[4-(1H-1,2,3-triazol-1-yl)phenyl]-2(1H, 3H)-imidazolone (2.72 g) and 1-methyl-2-pyrrolidone (100 ml) was added sodium hydride (70% in oil, 0.40 g), and the mixture was stirred at room temperature for 1 hour. (2R, 3S)-2-(2,4-Difluorophenyl)-3-methyl-2-(1H-1,2,4-triazol-1-yl)methyloxirane (2.51 g) was added thereto, and the mixture was stirred at 100° C. for 8 hours under an argon atmosphere. After cooling, the reaction solution was diluted with ethyl acetate (400 ml), and washed with water (100 ml), 1N-hydrochloric acid (100 ml×2) and a saturated aqueous solution of sodium chloride (50 ml) successively. The ethyl acetate layer was dried over anhydrous magnesium sulfate and concentrated under reduced pressure. The residue was purified by silica gel chromatography (eluent: ethyl acetate to ethyl acetate/acetone=5/1) and recrystallized from ethyl acetate-diisopropyl ether to give 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2(1H,3H)-imidazolone (Compound 11; 1.82 g) as a pale yellow crystalline powder.

mp: 178–181° C. $^1$H-NMR (CDCl$_3$)δ: 1.22(3H,d,J=7 Hz), 4.22 (1H,d,J=14.4 Hz), 5.01 (1H,q,J=7 Hz), 5.12 (1H,d,J=14.4 Hz), 5.38 (1H,br), 6.70–6.88 (4H,m), 7.40–7.55 (1H, m), 7.76 (1H,s), 7.80–7.93 (6H,m), 8.03 (1H,s); Elemental analysis for $C_{23}H_{20}F_2N_8O_2$; Calcd (%): C,57.74; H,4.21; N,23.42. Found (%): C,57.46; H,4.25; N,23.30. IR(KBr): 1691, 1656, 1619, 1527, 1502,1430 cm$^{-1}$.

WORKING EXAMPLE 12

1-[(1R,2R)-2-(2,4-Difluorophenyl)-2-hydroxy-1-methyl-3-(1H-1,2,4-triazol-1-yl)propyl]-3-[4-(1H-1,2,3-triazol-1-yl)phenyl]-2(1H,3H)-imidazolone (0.80 g) obtained in Working Example 11 was subjected to catalytic hydrogenation in the same manner as in Working Example 10 to give 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (Compound 12; 0.69 g).
Colorless crystalline powder
$^1$H-NMR (CDCl$_3$)δ: 1.08(3H,d,J=7 Hz), 3.70–4.14 (4H, m), 4.52 (1H,d,J=14.2 Hz), 4.60–4.78 (1H,m), 5.12 (1H,d, J=14.2 Hz), 5.38 (1H,br), 6.70–6.86 (2H,m), 7.35–7.50 (1H,m), 7.68–7.82 (4H,m), 7.77 (1H,s), 7.86 (2H,s), 7.97 (1H,s) Elemental analysis for $C_{23}H_{22}F_2N_8O_2$; Calcd (%): C,57.50; H,4.62; N,23.32. Found (%): C,57.38; H,4.59; N,23.41. IR(KBr): 1697, 1664, 1618, 1527, 1502,1427 cm$^{-1}$.

WORKING EXAMPLE 13

(2R,3S)-2-(2,4-Difluorophenyl)-3-methyl-2-(1H-1,2,4-triazol-1-yl)methyloxirane (2.51 g) was reacted with 1-[4-(2H-1,2,3-triazol-2-yl)phenyl]-2(1H,3H)-imidazolone (2.72 g) in the same manner as in Working Example 11 to give 1-[(1R,2R)-2-(2,4-difluorophenyl)-2-hydroxy-1-methyl-3-(1H-1,2,4-triazol-1-yl)propyl]-3-[4-(2H-1,2,3-triazol-2-yl)phenyl]-2(1H,3H)-imidazolone (Compound 13; 1.41 g).
Pale yellow needles
mp: 182–185° C. $^1$H-NMR (CDCl$_3$)δ: 1.22(3H,d,J=7 Hz), 4.22 (1H,d,J=14.4 Hz), 4.99 (1H,q,J=7 Hz), 5.01 (1H,d,J=14.4 Hz), 5.13 (1H,br), 6.70–6.88 (4H,m), 7.40–7.56 (1H, m), 7.75 (1H,s), 7.81 (2H,d,J=9.2 Hz), 7.84 (2H,s), 7.86 (1H,s), 8.18 (2H,d,J=9.2 Hz); Elemental analysis for $C_{23}H_{20}F_2N_8O_2$; Calcd (%): C,57.74; H,4.21; N,23.42. Found (%): C,57.67; H,4.20; N,23.59. IR(KBr): 3328, 1664, 1614, 1519, 1430, 1384 cm$^{-1}$.

WORKING EXAMPLE 14

1-[(1R,2R)-2-(2,4-Difluorophenyl)-2-hydroxy-1-methyl-3-(1H-1,2,4-triazol-1-yl)propyl]-3-[4-(2H-1,2,3-triazol-2-yl)phenyl]-2(1H,3H)-imidazolone (0.80 g) obtained in Working Example 13 was subjected to catalytic hydrogenation in the same manner as in Working Example 10 to give 1-[(1R,2R)-2-(2,4-difluorophenyloy)-2-hydroxy-1-methyl-3-(1H- 1,2,4-triazol-1-yl)propyl]-3-[4-(2H-1,2,3-triazol-2-yl)phenyl]-2-imidazolidinone (Compound 14; 0.70 g).
Colorless crystalline powder
mp: 196–197° C. $^1$H-NMR (CDCl$_3$)δ: 1.08(3H,d,J=7.4 Hz), 3.68–4.12 (4H,m), 4.53 (1H,d,J=14 Hz), 4.58–4.76 (1H,m), 5.13 (1H,d,J=14 Hz), 5.42 (1H,br), 6.70–6.85 (2H, m), 7.36–7.50 (1H,m), 7.71 (2H,d,J=9 Hz), 7.76 (1H,s), 7.81 (2H,s), 7.87 (1H,s), 8.07 (2H,d,J=9 Hz). IR(KBr): 3426, 1687, 1658, 1616, 1517, 1484 cm$^{-1}$.

WORKING EXAMPLE 15

(2R,3S)-2-(2,4.-Difluorophenyl)-3-methyl-2-(1H-1,2,4-triazol-1-yl)methyloxirane was reacted with 1-[4-(1H-1-pyrazolyl)phenyl]-2(1H,3H)-imidazolone in the same manner as in Working Example 11 to give 1-[(1R,2R)-2-(2,4-difluorophenyl)-2-hydroxy-1-methyl-3-(1H-1,2,4-triazol-1-yl)propyl]-3-[4-(1H-1-pyrazolyl)phenyl]-2(1H,3H)-imidazolone (Compound 15).
$^1$H-NMR (CDCl$_3$)δ: 1.21(3H,d,J=7 Hz), 4.22 (1H,d,J=14.4 Hz), 4.98 (1H,q,J=7 Hz), 5.12 (1H,d,J=14.4 Hz), 5.56 (1H,br), 6.47–6.54 (1H,m), 6.68–6.88 (4H,m), 7.40–7.56 (1H,m), 7.70–7.85 (6H,m), 7.85 (1H,s), 7.94 (1H,d,J=2.4 Hz); Elemental analysis for $C_{24}H_{21}F_2N_7O_2$; Calcd (%): C,60.37; H,4.43; N,20.53. Found (%): C,60.29; H,4.42; N,20.50.

WORKING EXAMPLE 16

1-[(1R,2R)-2-(2,4-Difluorophenyl)-2-hydroxy-1-methyl-3-(1H-1,2,4-triazol-1-yl)propyl]-3-[4-(1H-1-pyrazolyl)phenyl]-2(1H,3H)-imidazolone (Compound 15) obtained in Working Example 15 was subjected to catalytic hydrogenation in the same manner as in Working Example 10 to give 1-[(1R,2R)-2-(2,4-difluorophenyl)-2-hydroxy-1-methyl-3-(1H-1,2,4-triazol-1—,yl)propyl]-3-[4-(1H-1-pyrazolyl)phenyl]-2-imidazolidinone (Compound 16).
$^1$H-NMR (CDCl$_3$)δ: 1.08 (3H,d,J=7 Hz), 3.65–4.10 (4H, m), 4.53 (1H,d,J=14.2 Hz), 4.55–4.75(1H,m), 5.12 (1H,d, J=14.2 Hz), 5.45 (1H,br), 6.46–6.48 (1H,m), 6.70–6.85 (2H,m), 7.35–7.50 (1H,m), 7.60–7.75 (5H,m), 7.76 (1H,s), 7.88 (1H,s), 7.90 (1H,d,J=2.6 Hz); Elemental analysis for $C_{24}H_{23}F_2N_7O_2$; Calcd (%): C,60.12; H,4.83; N,20.45. Found (%): C,60.02; H,4.95; N,20.34.

WORKING EXAMPLE 17

(2R,3S)-2-(2,4-Difluorophenyl)-3-methyl-2-(1H-1,2,4-triazol-1-yl)methyloxirane was reacted with 1-[4-(1H-1,2,4-triazol-1-ylmethyl)phenyl]-2(1H,3H)-imidazolone in the same manner as in Working Example 11 to give 1-[(1R,2R)-2-(2,4-difluorophenyl)-2-hydroxy-1-methyl-3-(1H-1,2,4-triazol-1-yl)propyl]-3-[4-(1H-1,2,4-triazol-1-ylmethyl)phenyl]-2(1H,3H)-imidazolone (Compound 17).
$^1$H-NMR (CDCl$_3$)δ: 1.20 (3H,d,J=7 Hz), 4.19 (1H,d,J=14.4 Hz), 4.97 (1H,q,J=7 Hz), 5.10 (1H,d,J=14.4 Hz), 5.37 (2H,s), 5.55 (1H,br), 6.65 (1H,d,J=3.2 Hz), 6.70–6.90 (3H, m), 7.37 (2H,d,J=8.6 Hz), 7.35–7.55 (1H,m), 7.69 (2H,d,J=8.6 Hz), 7.74 (1H,s), 7.85 (1H,s), 7.99 (1H,s), 8.10 (1H,s).

WORKING EXAMPLE 18

(2R,3S)-2-(2,4-Difluorophenyl)-3-methyl-2-(1H-1,2,4-triazol-1-yl)methyloxirane was reacted with 4-t4-(1H-1,2,4-triazol-1-ylmethyl)phenyl]-3(2H,4H)-1,2,4-triazolone in the same manner as in Working Example 11 to give 2-[(1R,2R)-2-(2,4-difluorophenyl)-2-hydroxy-1-methyl-3-(1H-1,2,4-triazol-1-yl)propyl]-4-[4-(1H-1,2,4-triazol-1-ylmethyl)-phenyl]-3(2H,4H)-1,2,4-triazolone (Compound 18).
$^1$H-NMR (CDCl$_3$)δ: 1.30 (3H,d,J=7.2 Hz), 4.36 (1H,d,J=14.2 Hz), 5.02 (1H,d,J=14.2 Hz), 5.09 (1H,q,J=7.2 Hz), 5.42 (2H,s), 5.43 (1H,s), 6.75–6.90 (2H,m), 7.43 (2H,d,J=8.6 Hz), 7.50–7.67 (1H,m), 7.63 (2H,d,J=8.6 Hz), 7.69 (1H,s), 7.82 (1H,s), 7.94 (1H,s), 8.01 (1H,s), 8.15 (1H,s).

WORKING EXAMPLE 19

(2R,3S)-2-(2,4-Difluorophenyl)-3-methyl-2-(1H-1,2,4-triazol-1-yl)methyloxirane was reacted with 4-[4-(1H-1- pyrazolyl)phenyl]-3(2H,4H)-1,2,4-triazolone in the same manner as in Working Example 11 to give 2-[(1R,2R)-2-(2,4-difluorophenyl)-2-hydroxy-1-methyl-3-(1H-1,2,4-triazol-1-yl)propyl]-4-[4-(1H-1-pyrazolyl)phenyl]-3(2H,4H)-1,2,4-triazolone (Compound 19).

$^1$H-NMR (CDCl$_3$)δ: 1.32 (3H,d,J=7 Hz), 4.38 (1H,d,J=14.4 Hz), 5.05 (1H,d,J=14.4 Hz), 5.11 (1H,q,J=7 Hz), 5.45 (1H,s), 6.52–6.54 (1H,m), 6.76–6.90 (2H,m), 7.50–7.65 (1H,m), 7.65–7.93 (7H,m), 7.96 (1H,s), 7.98 (1H,d,J=2.6 Hz).

WORKING EXAMPLE 20

(2R,3S)-2-(2,4-Difluorophenyl)-3-methyl-2-(1H-1,2,4-triazol-1-yl)methyloxirane was reacted with 1-[4-(2H-1,2,3-triazol-2-ylmethyl)phenyl]-2(1H,3H)-imidazolone in the same manner as in Working Example 11 to give 1-[(1R,2R)-2-(2,4-difluorophenyl)-2-hydroxy-1-methyl-3-(1H-1,2,4-triazol-1-yl)propyl]-3-[4-(2H-1,2,3-triazol-2-ylmethyl)phenyl]-_2(1H,3H)-imidazolone (Compound 20).

$^1$H-NMR (CDCl$_3$)δ: 1.19 (3H,d,J=7 Hz), 4.17 (1H,d,J=14.4 Hz), 4.95 (1H,q,J=7 Hz), 5.09 (1H,d,J=14.4 Hz), 5.55 (1H,br), 5.63 (2H,s), 6.63 (1H,d,J=3.2 Hz), 6.70–6.86 (3H,m), 7.40–7.55 (1H,m), 7.42 (2H,d,J=8.6 Hz), 7.64 (2H,s), 7.64 (2H,d,J=8.6 Hz), 7.73 (1H,s), 7.85 (1H,s).

WORKING EXAMPLE 21

(2R,3S)-2-(2,4-Difluorophenyl)-3-methyl-2-(1H-1,2,4-triazol-1-yl)methyloxirane was reacted with 4-[4-(2H-1,2,3-triazol-2-ylmethyl)phenyl]-3(2H,4H)-1,2,4-triazolone in the same manner as in Working Example 11 to give 2-[(1R,2R)-2-(2,4-difluorophenyl)-2-hydroxy-1-methyl-3-(1H-1,2,4-triazol-1-yl)propyl]-4-[4-(2H-1,2,3-triazol-2-ylmethyl)phenyl]-3(2H,4H)-1,2,4-triazolone (Compound 21).

$^1$H-NMR (CDCl$_3$)δ: 1.29 (3H,d,J=7 Hz), 4.34 (1H,d,J=14.4 Hz), 5.02 (1H,d,J=14.4 Hz), 5.08 (1H,q,J=7 Hz), 5.44 (1H,s), 5.66 (2H,s), 6.73–6.87 (2H,m), 7.46 (2H,d,J=8.6 Hz), 7.50–7.62 (1H,m), 7.58 (2H,d,J=8.6 Hz), 7.66 (2H,s), 7.68 (1H,s), 7.78 (1H,s), 7.94 (1H,s); Elemental analysis for C$_{23}$H$_{21}$F$_2$N$_9$O$_2$; Calcd (%): C,55.98; H,4.29; N,25.55. Found (%): C,55.87; H,4.18; N,25.42.

WORKING EXAMPLE 22

(2R,3S)-2-(2,4-Difluorophenyl)-3-methyl-2-(1H-1,2,4-triazol-1-yl)methyloxirane was reacted with 4-[4-(1H-1-imidazolyl)phenyl]-3(2H,4H)-1,2,4-triazolone in the same manner as in Working Example 11 to give 2-[(1R,2R)-2-(2,4-difluorophenyl)-2-hydroxy-1-methyl-3-(1H-1,2,4-triazol-1-yl)propyl]-4-[4-(1H-1-imidazolyl)phenyl]-3(2H,4H)-1,2,4-triazolone (Compound 22).

$^1$H-NMR (CDCl$_3$)δ: 1.32 (3H,d,J=7 Hz), 4.40 (1H,d,J=14 Hz), 5.03 (1H,d,J=14 Hz), 5.11 (1H,q,J=7 Hz), 5.42 (1H,s), 6.73–6.88 (2H,m), 7.26 (1H,s), 7.33 (1H,s), 7.51–7.65 (1H,m), 7.57 (2H,d,J=9 Hz), 7.71 (1H,s), 7.76 (2H,d,J=9 Hz), 7.86 (1H,s), 7.91 (1H,s), 7.95 (1H,s).

WORKING EXAMPLE 23

(2R,3S)-2-(2,4-Difluorophenyl)-3-methyl-2-(1H-1,2,4-triazol-1-yl)methyloxirane was reacted with 1-[4-(1H-1-imidazolyl)phenyl]-2(1H,3H)-imidazolone in the same manner as in Working Example 11 to give 1-[(1R,2R)-2-(2,4-difluorophenyl)-2-hydroxy-1-methyl-3-(1H-1,2,4-triazol-1-yl)propyl]-3-[4-(1H-1-imidazolyl)phenyl]-2(1H,3H)-imidazolone (Compound 23).

$^1$H-NMR (CDCl$_3$)δ: 1.21 (3H,d,J=7 Hz), 4.22 (1H,d,J=14 Hz), 5.00 (1H,q,J=7 Hz), 5.12 (1H,d,J=14 Hz), 5.56 (1H,br), 6.70 (1H,d,J=3 Hz), 6.76–6.86 (3H,m), 7.23 (1H,s), 7.30 (1H,s), 7.42–7.54 (1H,m), 7.49 (2H,d,J=8 Hz), 7.75 (1H,s), 7.78 (1H,s), 7.84 (2H,d,J=8 Hz), 7.86 (1H,s).

WORKING EXAMPLE 24

1-[(1R,2R)-2-(2,4-Difluorophenyl)-2-hydroxy-1-methyl-3-(1H-1,2,4-triazol-1-yl)propyl]-3-[4-(1H-imidazolyl)phenyl]-2(1H,3H)-imidazolone (Compound 23) obtained in Working Example 23 was subjected to catalytic hydrogenation in the same manner as in Working Example 10 to give 1-[(1R,2R)-2-(2,4-difluorophenyl)-2-hydroxy-1-methyl-3-(1H-1,2,4-triazol-1-yl)propyl]-3-[4-(1H-1-imidazolyl)phenyl]-2-imidazolidinone (Compound 24).

$^1$H-NMR (CDCl$_3$)δ: 1.08 (3H,d,J=7 Hz), 3.70–4.08 (4H,m), 4.52 (1H,d,J=14 Hz), 4.55–4.76 (1H,m), 5.11 (1H,d,J=14 Hz), 5.40 (1H,br), 6.73–6.84 (2H,m), 7.20 (1H,s), 7.26 (1H,s), 7.36–7.50 (1H,m), 7.39 (2H,d,J=9 Hz), 7.69 (2H,d,J=9 Hz), 7.76 (1H,s), 7.82 (1H,s), 7.87 (1H,s).

WORKING EXAMPLE 25

(2R,3S)-2-(2,4-Difluorophenyl)-3-methyl-2-(1H-1,2,4-triazol-1-yl)methyloxirane was reacted with 4-t4-(2H-2-tetrazolyl)phenyl]-3(2H,4H)-1,2,4-triazolone in the same manner as in Working Example 11 to give 2-[(1R,2R)-2-(2,4-difluorophenyl)-2-hydroxy-1-methyl-3-(1H-1,2,4-triazol-1-yl)propyl]-4-[4-(2H-2-tetrazolyl)phenyl]-3(2H,4H)-1,2,4-triazolone (Compound 25).

$^1$H-NMR (CDCl$_3$)δ: 1.33 (3H,d,J=7 Hz), 4.40 (1H,d,J=14 Hz), 5.04 (1H,d,J=14 Hz), 5.11 (1H,q,J=7 Hz), 5.37 (1H,s), 6.77–6.88 (2H,m), 7.52–7.64 (1H,m), 7.71 (1H,s), 7.87 (2H,d,J=9 Hz), 7.92 (1H,s), 7.95 (1H,s), 8.34 (2H,d,J=9 Hz), 8.71 (1H,s); Elemental analysis for C$_{21}$H$_{18}$F$_2$N$_{10}$O$_2$; Calcd (%): C,52.50; H,3.78; N,29.15; Found (%): C,52.36; H,3.85; N,29.02.

WORKING EXAMPLE 26

(2R,3S)-2-(2,4-difluorophenyl)-3-methyl-2-(1H-1,2,4-triazol-1-yl)methyloxirane was reacted with 1-[4-(2H-2-tetrazolyl)phenyl]-2(1H,3H)-imidazolone in the same manner as in Working Example 11 to give 1-[(1R,2R)-2-(2,4-difluorophenyl)-2-hydroxy-1-methyl-3-(1H-1,2,4-triazol-1-yl)propyl]-3-[4-(2H-2-tetrazolyl)phenyl]-2(1H,3H)-imidazolone (Compound 26).

$^1$H-NMR (CDCl$_3$)δ: 1.21 (3H,d,J=7 Hz), 4.22 (1H,d,J=14 Hz), 5.02 (1H,q,J=7 Hz), 5.12 (1H,d,J=14 Hz), 5.49 (1H,br), 6.75 (1H,d,J=3 Hz), 6.75–6.85 (2H,m), 6.85 (1H,d,J=3 Hz), 7.42–7.54 (1H,m), 7.76 (1H,s), 7.85 (1H,s), 7.93 (2H,d,J=9 Hz), 8.25 (2H,d,J=9 Hz), 8.68 (1H,s).

WORKING EXAMPLE 27

1-[(1R,2R)-2-(2,4-Difluorophenyl)-2-hydroxy-1-methyl-3-(1H-1,2,4-triazol-1-yl)propyl]-3-[4-(2H-2-tetrazolyl)phenyl]-2(1H,3H)-imidazolone (Compound 26) obtained in Working Example 26 was subjected to catalytic hydrogenation in the same manner as in Working Example 10 to give 1-[(1R,2R)-2-(2,4-difluorophenyl)-2-hydroxy-1-methyl-3-(1H-1,2,4-triazol-1-yl)propyl]-3-[4-(2H-2-tetrazolyl)phenyl]-2-imidazolidinone (Compound 27).

$^1$H-NMR (CDCl$_3$)δ: 1.08 (3H,d,J=7 Hz), 3.69–3.81 (1H,m), 3.94–4.10 (3H,m), 4.52 (1H,d,J=14 Hz), 4.62–4.80 (1H,m), 5.13 (1H,d,J=14 Hz), 5.25–5.50 (1H,br), 6.72–6.84 (2H,m), 7.36–7.49 (1H,m), 7.77 (1H,s), 7.80 (2H,d,J=9 Hz), 7.86 (1H,s), 8.13 (2H,d,J=9 Hz), 8.64 (1H,s).

WORKING EXAMPLE 28

(2R,3S)-2-(2,4-Difluorophenyl)-3-methyl-2-(1H-1,2,4-triazol-1-yl)methyloxirane was reacted with 1-[4-(1H-1,2,3- triazol-1-ylmethyl)phenyl]-2(1H,3H)-imidazolone in the same manner as in Working Example 11 to give 1-[(1R,2R)-2-(2,4-difluorophenyl)-2-hydroxy-1-methyl-3-(1H-1,2,4-triazol-1-yl)propyl]-3-[4-(1H-1,2,3-triazol-1-ylmethyl)phenyl]-2(1H,3H)-imidazolone (Compound 28).

$^1$H-NMR (CDCl$_3$)δ: 1.20 (3H,d,J=7 Hz), 4.19 (1H,d,J=14 Hz), 4.97 (1H,q,J=7 Hz), 5.09 (1H,d,J=14 Hz), 5.55 (1H,br), 5.59 (2H,s), 6.65 (1H,d,J=3.2 Hz), 6.75–6.90 (3H,m), 7.35–7.55 (4H,m), 7.66–7.75 (4H,m), 7.84 (1H,s).

WORKING EXAMPLE 29

(2R,3S)-2-(2,4-Difluorophenyl)-3-methyl-2-(1H-1,2,4-triazol-1-yl)methyloxirane was reacted with 4-[4-(1H-1,2,3-triazol-1-ylmethyl)phenyl]-3(2H,4H)-1,2,4-triazolone in the same manner as in Working Example 2 to give 2-[(1R,2R)-2-(2,4-difluorophenyl)-2-hydroxy-1-methyl-3-(1H-1,2,4-triazol-1-yl)propyl]-4-[4-(1H-1,2,3-triazol-1-ylmethyl)phenyl]-3(2H,4H)-1,2,4-triazolone (Compound 29).

$^1$H-NMR (CDCl$_3$)δ: 1.30 (3H,d,J=7 Hz), 4.36 (1H,d,J=14 Hz), 5.00 (1H,d,J=14 Hz), 5.08 (1H,q,J=7 Hz), 5.41 (1H,s), 5.63 (2H,s), 6.75–6.90 (2H,m), 7.40–7.64 (6H,m), 7.69 (1H,s), 7.76 (1H,s), 7.80 (1H,s), 7.94 (1H,s).

WORKING EXAMPLE 30

(2R,3S)-2-(2,4-Difluorophenyl)-3-methyl-2-(1H-1,2,4-triazol-1-yl)methyloxirane was reacted with 1-[4-(2-methyl-4-thiazolyl)phenyl]-2(1H,3H)-imidazolone in the same manner as in Working Example 11 to give 1-[(1R,2R)-2-(2,4-difluorophenyl)-2-hydroxy-1-methyl-3-(1H-1,2,4-triazol-1-yl)propyl]-3-[4-(2-methyl-4-thiazolyl)phenyl]-2(1H,3H)-imidazolone (Compound 30).

$^1$H-NMR (CDCl$_3$)δ: 1.21 (3H,d,J=7 Hz), 2.78 (3H,s), 4.22 (1H,d,J=14 Hz), 4.98 (1H,q,J=7 Hz), 5.12 (1H,d,J=1.4 Hz), 5.60 (1H,br), 6.70–6.85 (4H,m), 7.33 (1H,s), 7.40–7.55 (1H,m), 7.69–8.00 (6H,m).

WORKING EXAMPLE 31

(2R,3S)-2-(2,4-Difluorophenyl)-3-methyl-2-(1H-1,2,4-triazol-1-yl)methyloxirane was reacted with 4-[4-(2-methyl-4-thiazolyl)phenyl]-3(2H,4H)-1,2,4-triazolone in the same manner as in Working Example 2 to give 2-[(1R,2R)-2-(2,4-difluorophenyl)-2-hydroxy-1-methyl-3-(1H-1,2,4-triazol-1-yl)propyl]-4-[4-(2-methyl-4-thiazolyl)phenyl]-3(2H,4H)-1,2,4-triazolone (Compound 31).

$^1$H-NMR (CDCl$_3$)δ: 1.31 (3H,d,J=7 Hz), 2.79 (3H,s), 4.37 (1H,d,J=14 Hz), 5.04 (1H,d,J=14 Hz), 5.11 (1H,q,J=7 Hz), 5.47 (1H,s), 6.77–6.90 (2H,m), 7.39 (1H,s), 7.50–7.70 (4H,m), 7.85–8.05 (4H,m).

WORKING EXAMPLE 32

(2R,3S)-2-(2-Fluorophenyl)-3-methyl-2-(1H-1,2,4-triazol-1-yl)methyloxirane was reacted with 1-[4-(1H-1,2,3-triazol-1-yl)phenyl]-2(1H,3H)-imidazolone in the same manner as in Working Example 11 to give 1-[(1R,2R)-2-(2-fluorophenyl)-2-hydroxy-1-methyl-3-(1H-1,2,4-triazol-1-yl)propyl]-3-[4-(1H-1,2,3-triazol-1-yl)phenyl3–2(1H,3H)-imidazolone (Compound 32).

$^1$-NMR (CDCl$_3$)δ: 1.21 (3H,d,J=7 Hz), 4.23 (1H,d,J=14.2 Hz), 5.08 (1H,q,J=7 Hz), 5.17 (1H,d,J=14.2 Hz), 5.36 (1H,br), 6.73 (1H,d,J=3.2 Hz), 6.86 (1H,d,J=3.2 Hz), 6.99–7.09 (2H,m), 7.19–7.52 (2H,m), 7.51–7.92 (6H,m), 7.80 (1H,s), 8.03 (1H,s); Elemental analysis for C$_{23}$H$_{21}$FN$_8$O$_2$; Calcd (%): C,59.99; H,4.60; N,24.23. Found (%): C,59.62; H,4.61; N,24.13.

WORKING EXAMPLE 33

(2R,3S)-2-(2-Fluorophenyl)-3-methyl-2-(1H-1,2,4-triazol-1-yl)methyloxirane was reacted with 1–14-(2H-1,2,3-triazol-2-yl)propyl]-2(1H,3H)-imidazolone to give 1-[(1R,2R)-2-(2-fluorophenyl)-2-hydroxy-1-methyl-3-(1H-1,2,4-triazol-1-yl)propoxy]-3-[4-(2H-1,2,3-triazol-2-yl)phenyl]-2(1H,3H)-imidazolone (Compound 33).

$^1$H-NMR (CDCl$_3$)δ: 1.21 (3H,d,J=7 Hz), 4.23 (1H,d,J=14 Hz), 5.07 (1H,q,J=7 Hz), 5.18 (1H,d,J=14 Hz), 5.37 (1H,br), 6.70 (1H,d,J=3.2 Hz), 6.83 (1H,d,J=3.2 Hz), 6.98–7.08 (2H,m), 7.19–7.51 (2H,m), 7.73 (1H,s), 7.75 (2H,d,J=9.2 Hz), 7.83 (2H,s), 7.85 (1H,s), 8.17 (2H,d,J=9.2 Hz); Elemental analysis for C$_{23}$H$_{21}$FN$_8$O$_2$; Calcd (%): C,59.99; H,4.60; N,24.33. Found (%): C,59.80; H,4.58; N,23.87.

WORKING EXAMPLE 34

1-[(1R,2R)-2-(2-Fluorophenyl)-2-hydroxy-1-methyl-3-(1H-1,2,4-triazol-1-yl)propyl]-3-[4-(1H-1,2,3-triazol-1-yl-)phenyl]-2(1H,3H)-imidazolone (compound 32) obtained in Working Example 32 was subjected to catalytic hydrogenation in the same manner as in Working Example 10 to give [(1R,2R)-2-(2-fluorophenyl)-2-hydroxy-1-methyl-3-(1H-1,2,4-triazol-1-yl)propyl]-3-[4-(1H-1,2,3-triazol-1-yl)phenyl]-2-imidazolidinone (Compound 34).

$^1$H-NMR (CDCl$_3$)δ: 1.08 (3H,d,J=7 Hz), 3.72–4.14 (4H, m), 4.54 (1H,d,J=14.2 Hz), 4.70–4.84 (1H,m), 5.17 (1H[]d,J=14.2 Hz), 5.30 (1H,br), 6.96–7.08 (2H,m), 7.18–7.50 (2H,m), 7.68–7.78 (4H,m), 7.75 (1H,s), 7.84 (2H,s), 7.98 (1H,s); Elemental analysis for C$_{23}$H$_{23}$FN$_8$O$_2$; Calcd (%): C,59.73; H,5.01; N,24.23. Found (%): C,59.32; H,4.99; N,24.00.

WORKING EXAMPLE 35

1-[(1R,2R)-2-(2-Fluorophenyl)-2-hydroxy-1-methyl-3-(1H-1,2,3-triazol-1-yl)propyl]-3-[4-(2H-1,2,3-triazol-2-yl)phenyl]-2(1H,3H)-imidazolone (Compound 33) obtained in Working Example 33 was subjected to catalytic hydrogenation in the same manner as in Working Example 10 to give 1-[(1R,2R)-2-(2-fluorophenyl)-2-hydroxy-1-methyl-3-(1H-1,2,4-triazol-1-yl)propyl]-3-[4-(2H-1,2,3-triazol-2-yl)phenyl]-2-imidazolidinone (Compound 35).

mp.: 178–179° C. $^1$H-NMR (CDCl$_3$)δ: 1.08 (3H,d,J=7 Hz), 3.71–4.07 (4H,m), 4.54 (1H,d,J=14 Hz), 4.74–4.77 (1H,m), 5.18 (1H,d,J=14 Hz), 5.38 (1H,br), 6.96–7.06 (2H, m), 7.16–7.51 (2H,m), 7.71 (2H,d,J=9 Hz), 7.74 (1H,s), 7.80 (2H,s), 7.83 (1H,s), 8.07 (2H,d,J=9 Hz); Elemental analysis for C$_{23}$H$_{23}$FN$_8$O$_2$; Calcd (%): C,59.73; H,5.01; N,24.23. Found (%): C,59.49; H,5.23; N,24.01.

WORKING EXAMPLE 36

(2R,3S)-2-(2,4-Difluorophenyl)-3-methyl-2-(1H-1,2,4-triazol-1-yl)methyloxirane (0.50 g), 4-[4-(2-methyl-4-oxazolyl)phenyl]-3(2H,4H)-1,2,4-triazolone (0.56 g) and potassium carbonate (powder: 1.38 g) were added to a mixture of 1-methyl-2-pyrrolidone (5 ml) and N,N-dimethylformamide(4 ml), and the mixture was heated with stirring at 90° C. for 20 hours. After cooling, the reaction solution was diluted with ethyl acetate (40 ml). Ice water (40 ml) was added thereto to separate the ethyl acetate layer. The ethyl acetate layer was washed with 0.5N-sodium hydroxide (40 ml), 1N-hydrochloric acid (40 ml) and a saturated aqueous solution of sodium chloride (40 ml) successively. The ethyl acetate layer was dried over anhydrous magnesium sulfate and distilled under reduced pressure to remove the solvent. The residue was purified by silica gel chromatography (eluent: ethyl acetate to ethyl acetate/methanol=9/1) and crystallized from ethyl acetate-diisopropyl ether to give 2-[(1R,2R)-2-(2,4-difluorophenyl)-2-hydroxy-1-methyl-3-(1H-1,2,4-triazol-1-yl)propyl]-4-[4-(2-methyl-4-oxazolyl)phenyl]-3(2H,4H)-1,2,4-triazolone (Compound 36, 0.33 g).

$^1$H-NMR (CDCl$_3$)δ: 1.31 (3H,d,J=7 Hz), 2.54 (3H,s), 4.36 (1H,d,J=14 Hz), 5.04 (1H,d,J=14 Hz), 5.10 (1H,q,J=7 Hz), 5.47 (1H,s), 6.77–6.88 (2H,m), 7.51–7.69 (4H,m), 7.85 (1H,s), 7.86 (2H,d,J=8 Hz), 7.88 (1H,s), 7.96 (1H,s).

WORKING EXAMPLE 37

(2R,3S)-2-(2,4-Difluorophenyl)-3-methyl-2-(1H-1,2,4-triazol-1-yl)methyloxirane was reacted with 1-[4-(2-methyl-4-oxazolyl)phenyl]-2(1H,3H)-imidazolone in the same manner as in Working Example 11 to give 1-[(1R,2R)-2-(2,4-difluorophenyl)-2-hydroxy-1-methyl-3-(1H-1,2,4-triazol-1-yl)propyl]-3-[4-(2-methyl-4-oxazolyl)phenyl]-2(1H,3H)-imidazolone (Compound 37).

$^1$H-NMR (CDCl$_3$)δ: 1.21 (3H,d,J=7 Hz), 2.53 (3H,s), 4.21 (1H,d,J=14 Hz), 4.97 (1H,q,J=7 Hz), 5.12 (1H,d,J=14 Hz), 5.60 (1H,br), 6.69–6.86 (4H,m), 7.42–7.55 (1H,m), 7.69 (2H,d,J=9 Hz), 7.73 (1H,s), 7.80 (2H,d,J=9 Hz), 7.84 (1H,s), 7.86 (1H,s).

WORKING EXAMPLE 38

(2R,3S)-2-(2-fluorophenyl)-3-methyl-2-(1H-1,2,4-triazol-1-yl)methyloxirane (2.24 g), 1-[4-(1H-1,2,4-triazol-1-yl)phenyl]-2(1H,3H)-imidazolone (2.17 g) and cesium carbonate (powder: 7.76 g) were added to dimethylsulfoxide (100 ml), and the mixture was heated with stirring at 100° C. for 17 hours. After being cooled, the reaction solution was diluted with ethyl acetate (200 ml). Ice water (200 ml) was added thereto to separate the ethyl acetate layer. The aqueous layer was extracted with ethyl acetate (100 ml). The ethyl acetate layers were combined and washed with 0.5N-sodium hydroxide (100 ml), 1N-hydrochloric acid (100 ml×2) and a saturated aqueous solution of sodium chloride (100 ml) successively. The ethyl acetate layer was dried over anhydrous magnesium sulfate and distilled under reduced pressure to remove the solvent. The residue was purified by silica gel chromatography (eluent: ethyl acetate/acetone=4/1) to give 1-[(1R,2R)-2-(2-fluorophenyl)-2-hydroxy-1-methyl-3-(1H-1,2,4-triazol-1-yl)propyl]-3-[4-[1H-1,2,4-triazol-1-yl)phenyl]-2(1H,3H)-imidazolone (Compound 38; 0.45 g).

$^1$H-NMR (CDCl$_3$)δ: 1.21 (3H,d,J=7 Hz), 4.23 (1H,d,J=14 Hz), 5.02 1H,q,J=7 Hz), 5.17 (1H,d,J=14 Hz), 5.37 (1H,br), 6.71 (1H,d,J=3.2 Hz), 6.86 (1H,d,J=3.2 Hz), 6.99–7.10 (2H,m), 7.20–7.52 (2H,m), 7.70–7.89 (6H,m), 8.13 (1H,s), 8.58 (1H,s).

WORKING EXAMPLE 39

1-[(1R,2R)-2-(2-Fluorophenyl)-2-hydroxy-1-methyl-3-(1H-1,2,4-triazol-1-yl)propyl]-3-[4-(1H-1,2,4-triazol-!1-yl)phenyl]-2(1H,3H)-imidazolone (Compound 38) obtained in Working Example 38 was subjected to catalytic hydrogenation in the same manner as in Working Example 10 to give 1-[(1R,2R)-2-(2-fluorophenyl)-2-hydroxy-1-methyl-3-(1H-1,2,4-triazol-1-yl)propyl]-3-[4-(1H-1,2,4-triazol-1-yl)phenyl]-2-imidazolidinone (Compound 39).

$^1$H-NMR (CDCl$_3$)δ: 1.08 (3H,d,J=7 Hz), 3.72–4.10 (4H, m), 4.53 (1H,d,J=14.2 Hz), 4.76–4.79(1H,m), 5.17 (1H,d, J=14.2 Hz), 5.19 (1H,br), 6.97–7.09 (2H,m), 7.17–7.46 (2H,m), 7.63–7.77 (5H,m), 7.82 (1H,s), 8.10 (1H,s), 8.52 (1H,s); Elemental analysis for C$_{23}$H$_{23}$FN$_8$O$_2$; Calcd (%): C,59.73; H,5.01; N,24.23. Found (%): C,59.33; H,5.03; N,23.98.

WORKING EXAMPLE 40

(2R,3S)-2-(2-Fluorophenyl)-3-methyl-2-(1H-1,2,4-triazol-1-yl)methyloxirane (2.34 g), 1-[4-(2H-2-tetrazolyl)-phenyl]-2(1H,3H)-imidazolone (2.28 g) and cesium carbonate (powder: 6.52 g) were added to 1-methyl-2-pyrrolidone (100 ml), and the mixture was heated at 80° C. for 18 hours with stirring. The reaction solution was cooled, diluted with * ethyl acetate (200 ml) and added to ice water (200 ml) to separate the ethyl acetate layer. The aqueous layer was extracted with ethyl acetate (100 ml). The combined ethyl acetate layers were washed with 1N-hydrochloric acid (100 ml×2) and a saturated aqueous solution of sodium chloride (100 ml) successively. The ethyl acetate layer was dried over anhydrous magnesium sulfate and distilled under reduced pressure to remove the solvent. The residue was purified by silica gel chromatography (eluent: hexane/acetone=1/1) to give 1-[(1R,2R)-2-(2-fluorophenyl)-2-hydroxy-1-methyl-3-(1H-1,2,4-triazol-1-yl)propyl]-3-[4-(2H-2-tetrazolyl) phenyl]-2(1H,3H)-imidazolone (Compound 40; 0.494 g) as a colorless crystalline powder.

$^1$H-NMR (CDCl$_3$)δ: 1.21 (3H,d,J=7 Hz), 4.23 (1H,d,J=14 Hz), 5.10 (1H,q,J=7 Hz), 5.19 (1H,d,J=14 Hz), 5.34 (1H,br), 6.75 (1H,d,J=3.2 Hz), 6.88 (1H,d,J=3.2 Hz), 6.99–7.09 (2H,m), 7.20–7.51 (2H,m), 7.75 (1H,s), 7.81.(1H,s-), 7.94 (2H d,J=9 Hz), 8.25 (2H,d,J=9 Hz), 8.68 (1H,s); Elemental analysis for C$_{22}$H$_{20}$FN$_9$O$_2$; Calcd (%): C,57.26; H,4.37; N,27.32. Found (%): C,57.19; H,4.29; N,27.07.

WORKING EXAMPLE 41

1-[(1R,2R)-2-(2-Fluorophenyl)-2-hydroxy-1-methyl-3-(1H-1,2,4-triazol-1-yl)propyl]-3-[4-(2H-2-tetrazolyl) phenyl]-2(1H,3H)-imidazolone (Compound 40) obtained in Working Example 40 was subjected to catalytic hydrogenation in the same manner as in Working Example 10 to give 1-[(1R,2R)-2-(2-fluorophenyl)-2-hydroxy-1-methyl-3-(1H-1,2,4-triazol-1-yl)propyl]-3-[4-(2H-2-tetrazolyl)phenyl]-2-imidazolidinone (Compound 41) as a colorless crystalline powder.

$^1$H-NMR (CDCl$_3$)δ: 1.08 (3H,d,J=7 Hz), 3.74–3.81 (1H, m), 3.94–4.13 (3H,m), 4.53 (1H,d,J=14 Hz), 4.63–4.81 (1H,m), 5.13 (1H,d,J=14 Hz), 5.15–5.30 (1H,br), 6.97–7.07 (2H,m), 7.17–7.45 (2H,m), 7.78 (1H,s), 7.79 (2H,d,J=9 Hz), 7.83 (1H,s), 8.13 (2H,d,J=9 Hz), 8.65 (1H,s); Elemental analysis for C$_{22}$H$_{22}$FN$_9$O$_2$; Calcd (%): C,57.01; H,4.78; N,27.20. Found (%): C,56.96; H,4.86; N,26.84.

WORKING EXAMPLE 42

72% sodium hydride in oil (17 mg) was dispersed in dimethylformamide (3 ml), to which 1,2,4-triazole (42 mg) was added at ice-bath temperature, and the mixture was stirred at room temperature for 40 minutes. To the resultant was added a solution of 1-[(1R, 2S)-2-(2,4-difluorophenyl)-2,3-epoxy-1-methylpropyl]-3-[4-[(1H-1-tetrazolyl)phenyl]-2H(1H,3H)-imidazolone (0.205 g) in dimethylformamide (2 ml), and the mixture was heated at 50° C. for 6 hours. After the mixture was cooled, cold water (30 ml) and ethyl acetate (30 ml) were added thereto. The separated aqueous layer was extracted with ethyl acetate twice. The combined ethyl acetate layers were washed with water and a saturated aqueous solution of sodium chloride successively, dried over anhydrous magnesium sulfate, and distilled under reduced pressure to remove the solvent. The residue was purified by silica gel chromatography (eluent: ethyl acetate) to give 1-[(1R,2R)-2-(2,4-difluorophenyl)-2-hydroxy-1-methyl-3-(1H-1,2,4-triazol-1-yl)propyl]-3-[4-(1H-1-tetrazolyl) phenyl]-2(1H,3H)-imidazolone (Compound.42; 0.15 g) as a colorless crystalline powder.

$^1$H-NMR (CDCl$_3$)δ: 1.21 (3H,d,J=7 Hz), 4.22 (1H,d,J=14 Hz), 5.03 (1H,q,J=7 Hz), 5.13 (1H,d,J=14 Hz), 5.45 (1H,br), 6.74–6.88 (4H,m), 7.42–7.55 (1H,m), 7.77 (1H,s), 7.82 (2H,d,J=9 Hz), 7.86 (1H,s), 7.96 (2H,d,J=9 Hz), 9.06 (1H,s).

The same product (Compound 42) was obtained when a reaction was carried out in the same manner as in the above except that sodium hydride was replaced by potassium carbonate.

WORKING EXAMPLE 43

1-[(1R,2R)-2-(2,4-Difluorophenyl)-2-hydroxy-1-methyl-3-(1H-1,2,4-triazol-1-yl)propyl]-3-[4-(1H-1-tetrazolyl)phenyl]-2(1H,3H)-imidazolone (compound 42) obtained in Working Example 42 was subjected to catalytic hydrogenation in the same manner as in Working Example 10 to give 1-[(1R,2R)-2-(2,4— difluorophenyl)-2-hydroxy-1-methyl-3-(1H-1,2,4-triazol-1-yl)propyl]-3-[4-(1H-1-tetrazolyl)phenyl]-2-imidazolidinone (compound 43) as a colorless crystalline powder.

$^1$H-NMR (CDCl$_3$)δ: 1.08 (3H,d,J=7 Hz), 3.69–4.14 (4H, m), 4.52 (1H,d,J=14 Hz), 4.65–4.80 (1H,m), 5.12 (1H,d,J=14 Hz), 5.35 (1H,br), 6.74–6.84 (2H,m), 7.36–7.49 (1H,m), 7;68 (2H,d,J=9 Hz), 7.77 (1H,s), 7.82 (2H,d,J=9 Hz), 7.87 (1H,s), 8.98 (1H,s).

WORKING EXAMPLE 44

72% sodium hydride in oil (120 mg) was dispersed in dimethylformamide (10 ml), to which 1,2,4-triazole (290 mg) was added at ice-bath temperature, and the mixture was stirred at room temperature for 30 minutes. To the resultant was added a solution of 1-[(1R, 2S)-2-(2-fluorophenyl)-2,3-epoxy-1-methylpropyl]-3-[4-[(1H-1-tetrazolyl)phenyl]-2H(1H,3H)-imidazolone (0.82 g) in dimethylformamide (5 ml), and the mixture was heated at 50° C. for 5 hours. After the reaction solution was cooled, cold water (30 ml) and ethyl acetate (40 ml) were added. The separated aqueous layer was extracted with ethyl acetate twice. The ethyl acetate layers were combined, washed with water and a saturated aqueous solution of sodium chloride successively, dried over anhydrous magnesium sulfate and distilled under reduced pressure to remove the solvent. The residue was purified by silica gel chromatography (eluent: ethyl acetate) to give 1-[(1R,2R)-2-(2-fluorophenyl)-2:-hydroxy-1-methyl-3-(1H-1,2,4-triazol-1-yl)propyl]-3-[4-(1H-1-tetrazolyl)phenyl]-2(1H,3H)-imidazolone (Compound 44; 0.30 g) as a colorless crystalline powder.

$^1$H-NMR (CDCl$_3$)δ: 1.21 (3H,d,J=7 Hz), 4.22 (1H,d,J=14 Hz), 5.10 (1H,q,J=7 Hz), 5.18 (1H,d,J=14 Hz), 5.31 (1H,br), 6.75 (1H,d,J=3 Hz), 6.90 (1H,d,J=3 Hz), 6.99–7.32 (3H,m), 7.43–7.51 (1H,m), 7.75 (1H,s), 7.80–7.85 (3H,m), 7.97 (2H,d,J=9 Hz), 9.07 (1H,s).

WORKING EXAMPLE 45

1-[(1R,2R)-2-(2-Fluorophenyl)-2-hydroxy-1-methyl-3-(1H-1,2,4-triazol-1-yl)propyl]-3-[4-(1H-1-tetrazolyl)phenyl]-2(1H,3H)-imidazolone (compound 44) obtained in Working Example 44 was subjected to catalytic hydrogenation in the same manner as in Working Example 10 to give 1-[(1R,2R)-2-(2-fluorophenyl)-2-hydroxy-1-methyl-3-(1H-1,2,4-triazol-1-yl)propyl]-3-[4-(1H-1-tetrazolyl)phenyl]-2-imidazolidinone (Compound 45).

$^1$H-NMR (CDCl$_3$)δ: 1.08 (3H,d,J=7 Hz), 3.70–4.19 (4H, m), 4.53 (1H,d,J=14 Hz), 4.72–4.88 (1H,m), 5.10–5.26 (2H,m), 6.97–7.45 (4H,m), 7.68 (2H,d,J=9 Hz), 7.76 (1H,s), 7.82 (1H,s), 7.83 (2H,d,J=9 Hz), 8.97 (1H,s).

WORKING EXAMPLE 46

1-[(1R,2S)-2-(2-Fluorophenyl)-2-hydroxy-3-methanesulfonyloxy-1-methylpropyl]-3-[4-(1H-1-tetrazolyl)phenyl]-2(1H,3H)-imidazolone (200 mg) was dissolved in dimethylformamide (10 ml), to which 1H-1,2,4-triazole (83 mg) and potassium carbonate (168 mg) were added, and the mixture was heated at 50° C. for 20 hours. The reaction solution was diluted with ethyl acetate (30 ml), washed with water (15 ml), 1N-hydrochloric acid (15 ml×2) and a saturated aqueous solution of sodium chloride (15 ml). The organic layer was dried over magnesium sulfate and distilled under reduced pressure to remove the solvent. The residue was purified by silica gel chromatography (eluent: ethyl acetate). The desired fraction was concentrated and recrystallized from a mixture of ethyl acetate and diisopropyl ether to give 1-[(1R,2R)-2-(2-fluorophenyl)-2-hydroxy-1-methyl-3-(1H-1,2,4-triazol-1-yl)propyl-3-[4-(1H-1-tetrazolyl)phenyl]-2(1H,3H)-imidazolone (Compound 44, 65 mg) as a colorless crystalline powder.

$^1$H-NMR (CDCl$_3$)δ: 1.21 (3H,d,J=7 Hz), 4.22 (1H,d,J=14 Hz), 5.11 (1H,q,J=7 Hz), 5.18 (1H,d,J=14 Hz), 5.32 (1H,br), 6.75 (1H,d,J=3 Hz), 6.90 (1H,d,J=3 Hz), 7.00–7.27 (3H,m), 7.43–7.51 (1H,m), 7.75 (1H,s), 7.80–7.84 (3H,m), 7.97 (2H,d,J=9 Hz), 9.06 (1H,s).

Tables 10 to 14 show a group of preferred compounds belonging to the compound (I) of the present invention but the present invention is not limited to those compounds.

TABLE 10

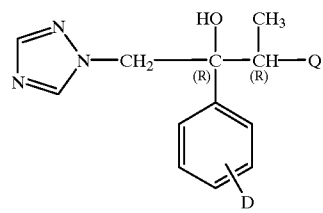

| Compound No. | D | Q |
|---|---|---|
| 1 | 2,4-F$_2$ | —N(triazolone)—C$_6$H$_4$—N(triazolone)—C$_6$H$_4$—OCH$_2$CF$_2$CF$_2$H |
| 2 | 2,4-F$_2$ | —N(triazolone)—C$_6$H$_4$—N(imidazolone)—C$_6$H$_4$—OCH$_2$CF$_2$CF$_2$H |

TABLE 10-continued

| Compound No. | D | Q |
|---|---|---|
| 3 | 2,4-F$_2$ | triazolone–C$_6$H$_4$–triazolone–C$_6$H$_4$–OCF$_2$CF$_2$H |
| 4 | 2,4-F$_2$ | triazolone–C$_6$H$_4$–triazolone–CH$_2$CF$_3$ |
| 5 | 2,4-F$_2$ | triazolone–C$_6$H$_4$–(1,2,4-triazol-1-yl) |
| 6 | 2,4-F$_2$ | triazolone–C$_6$H$_4$–(1,2,3-triazol-1-yl) |
| 7 | 2,4-F$_2$ | triazolone–C$_6$H$_4$–(2H-1,2,3-triazol-2-yl) |
| 8 | 2,4-F$_2$ | triazolone–C$_6$H$_4$–triazolone–CH$_2$CF$_2$CF$_2$H |
| 9 | 2,4-F$_2$ | imidazolone–C$_6$H$_4$–(1,2,4-triazol-1-yl) |
| 10 | 2,4-F$_2$ | imidazolidinone–C$_6$H$_4$–(1,2,4-triazol-1-yl) |

TABLE 11
| Compound No. | D | Q |
|---|---|---|
| 11 | 2,4-F$_2$ | 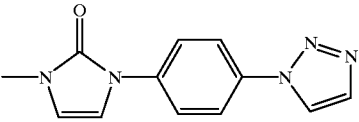 |
| 12 | 2,4-F$_2$ | 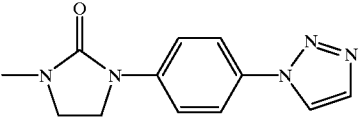 |
| 13 | 2,4-F$_2$ | 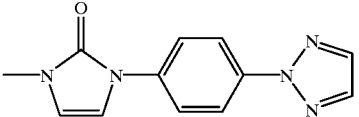 |
| 14 | 2,4-F$_2$ | 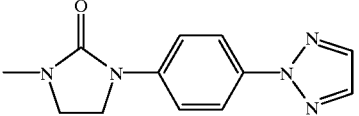 |
| 15 | 2,4-F$_2$ | 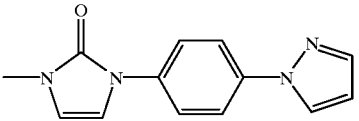 |
| 16 | 2,4-F$_2$ | 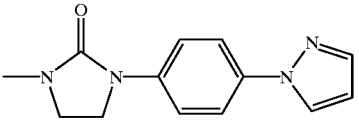 |
| 17 | 2,4-F$_2$ | 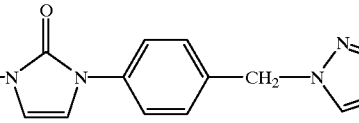 |
| 18 | 2,4-F$_2$ | 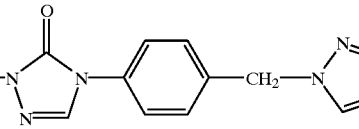 |
| 19 | 2,4-F$_2$ | 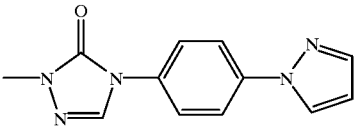 |
| 20 | 2,4-F$_2$ | 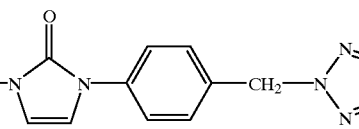 |
TABLE 12
| Compound No. | D | Q |
|---|---|---|
| 21 | 2,4-F$_2$ | 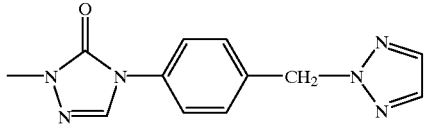 |
| 22 | 2,4-F$_2$ | 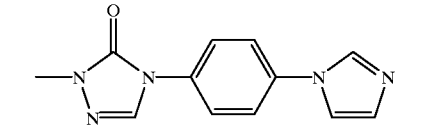 |
| 23 | 2,4-F$_2$ | 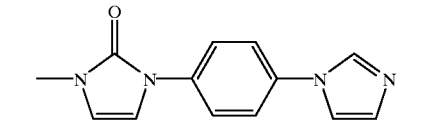 |
| 24 | 2,4-F$_2$ | 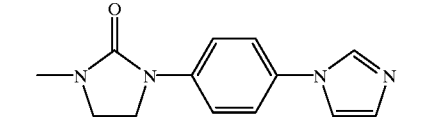 |
| 25 | 2,4-F$_2$ | 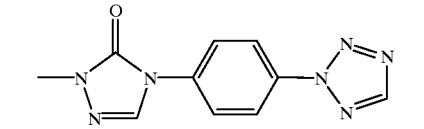 |
| 26 | 2,4-F$_2$ | 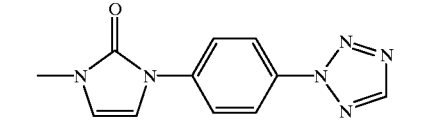 |
| 27 | 2,4-F$_2$ | 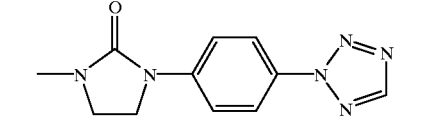 |
| 28 | 2,4-F$_2$ | 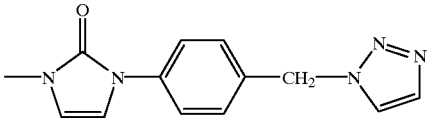 |
| 29 | 2,4-F$_2$ | 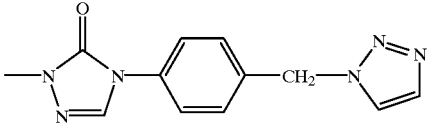 |
| 30 | 2,4-F$_2$ | 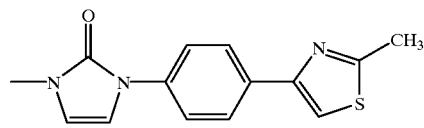 |

TABLE 13

| Compound No. | D | Q |
|---|---|---|
| 31 | 2,4-F$_2$ | (structure: triazolone-phenyl-thiazole-CH$_3$) |
| 32 | 2-F | (structure: imidazolone-phenyl-triazole) |
| 33 | 2-F | (structure: imidazolone-phenyl-triazole) |
| 34 | 2-F | (structure: imidazolone-phenyl-triazole) |
| 35 | 2-F | (structure: imidazolone-phenyl-triazole) |
| 36 | 2,4-F$_2$ | (structure: triazolone-phenyl-oxazole-CH$_3$) |
| 37 | 2,4-F$_2$ | (structure: imidazolone-phenyl-oxazole-CH$_3$) |
| 38 | 2-F | (structure: imidazolone-phenyl-triazole) |
| 39 | 2-F | (structure: imidazolone-phenyl-triazole) |

TABLE 14

| Compound No | D | Q |
|---|---|---|
| 40 | 2-F | (structure: imidazolone-phenyl-tetrazole) |
| 41 | 2-F | (structure: imidazolone-phenyl-tetrazole) |
| 42 | 2,4-F$_2$ | (structure: imidazolone-phenyl-tetrazole) |
| 43 | 2,4-F$_2$ | (structure: imidazolone-phenyl-tetrazole) |
| 44 | 2-F | (structure: imidazolone-phenyl-tetrazole) |
| 45 | 2-F | (structure: imidazolone-phenyl-tetrazole) |

FORMULATION EXAMPLE 1

All the components for the below prescription using the Compound 7 obtained in Working Example 7 were mixed, and filled into gelatine capsules to prepare capsuled drugs each containing Compound 7 in the amount of 50 mg. 112

| | |
|---|---|
| Compound 7 in Working Example 7 | 50 mg |
| Lactose | 100 mg |
| Corn Starch | 40 mg |
| Magnesium Stearate | 10 mg |
| Total | 200 mg |

FORMULATION EXAMPLE 2

The compound 10 obtained in Working Example 10 and magnesium stearate were made into granules by using an aqueous solution of soluble starch, dried and mixed with lactose and corn starch. The mixture was molded under compression to form a tablet for the below prescription.

| | |
|---|---|
| Compound 10 of Working Example 10 | 50 mg |
| Lactose | 65 mg |
| Corn Starch | 30 mg |

| -continued | |
|---|---|
| Soluble Starch | 35 mg |
| Magnesium Stearate | 20 mg |
| Total | 200 mg |

EXPERIMENT EXAMPLE 1

Test Method: Five-week-old Crj: $CDF_1$ mice were inoculated with the minimum lethal dose of *Candida albicans* TA intravenously. The test compounds were administered orally once immediately after infection as a 30% HPCD (hydroxypropyl-β-cyclodextrin) solution. The activity was expressed in terms of $ED_{50}$ value calculated by the Reed and Muench method from the survival rate 7 days after infection. Result: Tables 15 and 16 shows the protective effects of the present compounds against Candida albicans infection in mice.

TABLE 15

| Compound No. | $ED_{50}$ (mg/kg) PO |
|---|---|
| 5 | 0.22 |
| 6 | 0.35 |
| 7 | 0.096 |
| 9 | 0.16 |
| 10 | 0.32 |
| 11 | 0.45 |
| 12 | 0.71 |
| 13 | 0.18 |
| 14 | 0.32 |
| 19 | 0.39 |
| 25 | 0.088 |
| 26 | 0.16 |
| 27 | 0.18 |
| 34 | 0.80 |
| 35 | 0.71 |

PO: oral administration

TABLE 16

| Compound No. | $ED_{50}$ (mg/kg) PO |
|---|---|
| 38 | 0.5 |
| 39 | 0.5 |
| 40 | 0.35 |
| 41 | 0.80 |
| 42 | 0.22 |
| 43 | 0.89 |
| 44 | 0.39 |
| 45 | 0.45 |

PO: oral administration

Industrial Applicability

The present compounds or their salts have low toxicity and excellent antifungal activity. Therefore, they are useful in protection and treatment for fungal infections of mammals as antifungal preparations. In addition, they can serve as antifungal preparations for agricultural use.

What is claimed is:

1. A compound represented by the formula (I):

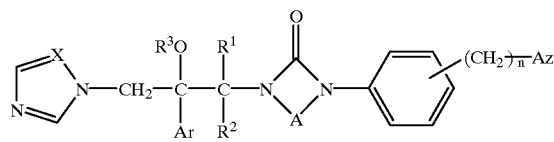

wherein Ar is a halophenyl group; one of $R^1$ and $R^2$ is a hydrogen atom and the other is a $C_{1-4}$ alkyl group; $R^3$ is a hydrogen atom; X is a nitrogen atom; A is $-CH_2-CH_2-$; n is an integer from 0 to 2; and Az is an azolyl group selected from the group consisting of

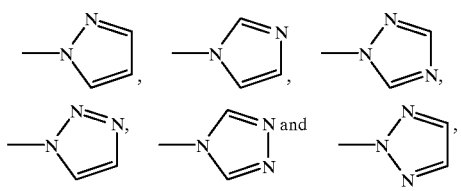

or a salt thereof.

2. A compound of claim 1 in which the carbon atom to which Ar is bonded is an (R)-configuration and the carbon atom to which $R^2$ is bonded is an (R)-configuration.

3. A compound of claim 1 in which Ar is a phenyl group substituted with one or two fluorine atoms.

4. A compound of claim 1 in which Ar is a 2-fluorophenyl group or a 2,4-difluorophenyl group.

5. A compound of claim 1 in which n is 0.

6. A compound of claim 1, wherein Az is an triazolyl group selected from the group consisting of

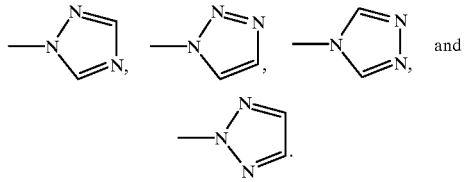

7. A compound of claim 1 which is 1-[(1R, 2R)-2-(2,4-di-fluorophenyl)-2-hydroxy-1-methyl-3-(1H-1,2,4-triazol-1-yl)propyl]-3-[4-(1H-1,2,4-triazol-1-yl)phenyl]-2-imidazolidinone or a salt thereof.

8. A compound of claim 1 which is 1-[(1R, 2R)-2-(2,4-di-fluorophenyl)-2-hydroxy-1-methyl-3-(1H-1,2,4-triazol-1-yl)propyl]-3-[4-(1H-1,2,3-triazol-1-yl)phenyl]-2-imidazolidinone or a salt thereof.

9. A pharmaceutical composition which comprises a pharmacologically effective amount of a compound of the formula (I) as defined in claim 1 or its pharmaceutically acceptable salt and one or more of a carrier and diluent.

10. A method for treatment of a fungal infection which comprises administration of a pharmacologically effective amount of a compound of the formula (I) as defined in claim 1 or its pharmaceutically acceptable salt.

11. A compound as claimed in claim 1, wherein Az is a 1,2,3-triazolyl group.

* * * * *